United States Patent [19]

Janoff et al.

[11] Patent Number: 5,616,334
[45] Date of Patent: Apr. 1, 1997

[54] LOW TOXICITY DRUG-LIPID SYSTEMS

[75] Inventors: Andrew S. Janoff, Yardley, Pa.;
Lawrence Boni, Monmouth Junction, N.J.; Thomas D. Madden; Pieter R. Cullis, both of Vancouver, Canada; Robert P. Lenk, Lambertville; John J. Kearns, Princeton, both of N.J.; Anthony G. Durning, Yardley, Pa.; Robert Klimchak, Flemington, N.J.; Joel Portnoff, Richboro, Pa.

[73] Assignee: The Liposome Company, Inc., Princeton, N.J.

[21] Appl. No.: 430,699

[22] Filed: Apr. 28, 1995

Related U.S. Application Data

[63] Continuation of Ser. No. 876,121, Apr. 29, 1992, abandoned, and a continuation-in-part of Ser. No. 164,580, Mar. 7, 1988, abandoned, and a continuation-in-part of Ser. No. 225,327, Jul. 28, 1988, abandoned, which is a continuation of Ser. No. 79,309, Jul. 29, 1987, abandoned, said Ser. No. 876,121, is a continuation of Ser. No. 236,700, Aug. 25, 1988, abandoned, which is a continuation-in-part of Ser. No. 136,267, Dec. 22, 1987, Pat. No. 4,963,297, said Ser. No. 164,580, is a continuation-in-part of Ser. No. 69,908, Jul. 6, 1987, abandoned, which is a continuation-in-part of Ser. No. 22,157, Mar. 5, 1987, abandoned.

[51] Int. Cl.$^6$ .................. A01N 25/32; A01N 57/26; A61K 31/685
[52] U.S. Cl. .................. 424/404; 264/4.1; 264/4.3; 264/4.6; 428/402.2; 436/164; 514/78
[58] Field of Search .................. 264/4.1, 4.3; 428/402.2; 424/450, 404; 436/829; 514/78, 967

[56] References Cited

U.S. PATENT DOCUMENTS

| | | | |
|---|---|---|---|
| 3,244,590 | 4/1966 | Schaffner et al. | 514/31 X |
| 3,993,754 | 11/1976 | Rahman et al. | 424/450 X |
| 4,145,410 | 3/1979 | Sears | 424/450 |
| 4,224,179 | 9/1980 | Schneider et al. | 264/4.6 |
| 4,229,360 | 10/1980 | Schneider et al. | 260/403 |
| 4,235,871 | 11/1980 | Papahadjopoulos et al. | 424/450 |
| 4,310,506 | 1/1982 | Baldeschwieler | 424/1.1 |
| 4,342,750 | 8/1982 | Gordon | 514/31 X |
| 4,358,442 | 11/1982 | Wirtz-Peitz et al. | 514/78 X |
| 4,372,949 | 2/1983 | Kodama et al. | 424/450 X |
| 4,419,348 | 12/1983 | Rahman et al. | 514/34 |
| 4,436,746 | 3/1984 | Renfroe | 514/411 |
| 4,460,577 | 7/1984 | Moro et al. | 424/450 |
| 4,508,703 | 4/1985 | Redziniak et al. | 424/450 |
| 4,522,803 | 6/1985 | Lenk et al. | 424/1.1 |
| 4,551,288 | 11/1985 | Kelly | 264/4.6 |
| 4,588,578 | 5/1986 | Fountain et al. | 424/1.1 |
| 4,604,376 | 8/1986 | Teng | 514/3 |
| 4,622,219 | 11/1986 | Haynes | 424/450 |
| 4,663,167 | 5/1987 | Lopez-Berestein et al. | 514/37 |
| 4,721,612 | 1/1988 | Janoff et al. | 424/1.1 |
| 4,766,046 | 8/1988 | Abra et al. | 424/450 |
| 4,812,312 | 3/1989 | Lopez-Berestein et al. | 424/417 |
| 4,822,777 | 4/1989 | Abra | 514/31 |
| 4,880,635 | 11/1989 | Janoff et al. | 424/450 |
| 4,897,384 | 1/1990 | Janoff et al. | 514/34 |
| 4,963,297 | 10/1990 | Madden | 264/4.3 |
| 4,973,465 | 11/1990 | Baurain et al. | 424/406 |
| 5,059,591 | 10/1991 | Janoff et al. | 514/31 |
| 5,077,056 | 12/1991 | Bally et al. | 424/450 |

FOREIGN PATENT DOCUMENTS

| | | |
|---|---|---|
| 202837 | 11/1986 | European Pat. Off. . |
| 0202837 | 11/1986 | European Pat. Off. . |
| 0260811 | 3/1988 | European Pat. Off. . |
| 0296845 | 6/1988 | European Pat. Off. . |
| 2607719 | 12/1986 | France .............. B01D 9/02 |
| 2611138 | 2/1987 | France .............. A61K 9/00 |
| 8712424 | 9/1987 | France . |
| 85/00968 | 3/1985 | WIPO . |
| 85/04578 | 10/1985 | WIPO . |
| 85/05030 | 11/1985 | WIPO . |
| 86/00238 | 1/1986 | WIPO . |
| 86/01103 | 2/1986 | WIPO . |
| 87/02219 | 4/1987 | WIPO . |

OTHER PUBLICATIONS

DeKruijff, et al. "Polyene Antibiotic–Sterol Interactions in Membranes of Acholephasma Laidlawii Cells and Lecithin Liposomes" BBA 339 (1974) 57–70.

Witzke, et al., "Dissociation Kinetics and Equilibrium Binding Properties of Polyene Antibiotic Complexes with Phosphatidylcholine/Sterol Vesicles" Biochemistry 23 (1984) 8, 1668–1674.

Dufourc et al., "Interaction of Amphotericin B. with Membrane Lipids as Viewed by H–NMR"; 1984; Biochimica et Biophysica Acta, 778 pp. 435–432.

Ahrens, et al., "Treatment of experimental murine candidiasis with liposome–associated amphotericin B", 1984; S. Jour. Med. Vet Mycol, 22:163–166.

Bangham, et al., "Diffusion of Univalent Iona Across the Lamellae of Swollen Phospholipids", 1965; J. Mol. Biol., 13:238–252.

(List continued on next page.)

Primary Examiner—Richard D. Lovering
Attorney, Agent, or Firm—Kenneth B. Rubin

[57] ABSTRACT

Methods and compositions are described for nonliposomal lipid complexes in association with toxic hydrophobic drugs such as the polyene antibiotic amphotericin B. Lipid compositions are preferably a combination of the phospholipids dimyristoylphosphatidylcholine (DMPC) and dimyristoylphosphatidylglycerol (DMPG) in about a 7:3 mole ratio. The lipid complexes contain a bioactive agent, and may be made by a number of procedures, at high drug:lipid ratios. These compositions of high drug:lipid complexes (HDLCs) may be administered to mammals such as humans for the treatment of infections, with substantially equivalent or greater efficacy and reduced drug toxicities as compared to the drugs in their free form. Also disclosed is a novel liposome-loading procedure, which may also be used in the formation of the HDLCs.

23 Claims, 17 Drawing Sheets

OTHER PUBLICATIONS

Barlett, et al., "Phosphorus Assay in Column Chromatography", 1959; J. Bio. Chem. 234:466–468.

Burke, et al., "Ligand self–association at the surface of liposomes: a complication during equilibrium–binding studies", Chem. Abstracts. vol. 102, No. 3 (1985).

Chapman, "Physicochemical Properties of Phospholipids and Lipid–Water Systems", in Liposome Technol., 1984; pp. 1–18.

Cullis, et al., "Structure Properties of Lipids and Their Functional Roles in Biological Membranes", 1983; in Membrane Fluidity in Biology, vol. 1, Academic Press.

Deamer, et al., "Lamellar and Hexagonal Lipid Phases Visualized by Freeze–Etching", 1970; Biochim, Biophys. Acta., 219:47–60.

Deamer, et al., "Permeability of Lipid Bilayers to Water and Ionic Solutes", 1986; Chem. and Phys. of Lipids 40:167–187.

Graybill, et al., "Treatment of Burine Cryptococcosis with Liposome–Associated Amphotericin B", 1982; J. Infec. Dis. 145:748–752.

Gruner, et al., "Novel Multilayered Lipid Vesicles: Comparison of Physical Characteristics of Multilamellar Liposomes and Stable Plurilamellar Vesicles", 1985; Biochem. 24:2833–2842.

Herbette, et al., "Comparisons of the interaction of propranolol and timotol with model and biological membrane systems", Chem. Abstracts vol. 99, No. 23 (1983).

Juliano, et al., "Selective Toxicity and Enhanced Therapeutic Index of Liposomal Polyene Antibiotics in Systemic Fungal Infections", 1985; Ann. N.Y. Acad. Sci. 446:390–402.

Koppel, "Analysis of Macromolecular Polydispersity in Intensity Correlation Spectroscopy: The Method of Cumulants", 1972; J. Chem. Phys. 4814–4820.

Lopez–Berestein, et al., "Liposomal Amphotericin B for the Treatment of Systemic Fungal Infections in Patients with Cancer: A Preliminary Study" 1985; J. Infect. Dis., 151:704–710.

Lopez–Berestein, et al., "Prophylaxis of *Candida albicans* Infection in Neutropenic Mice with Liposome–Encapsulated Amphotericin B", 1984; Antimicrob. Agents Chemo. 25(3):366–367.

Lopez–Berestein, et al., "Treatment and Prophylaxis of Disseminated Infection Due to *Candida albicans* in Mice iwth Liposome–Encapsulated Amphotericin B", 1983; J. Infec. Dis. 147:939–945.

Mayer, et al., "Solute distributions and trapping efficiencies observed in freeze–thawed multilamellar vesicles", 1985; Biochim. Biophys, Acta. 817:193–196.

Panosian, et al., "Treatment of Experimental Cutaneous Leishmaniasis with Liposome Intercalated Amphotericin B", 1984; 25:655–656.

Papahadjopoulos, et al., "Phospholipid Model Membranes", 1967; Biochim. Biophys. Acta., 135:624–638.

Payne, et al., "Characterization of Proliposomes", 1986; J. Pharm. Sci. 75:330–333.

Schaffner, et al., "Anti–viral activity of amphotericin B methyl ester: inhibition of HTLV–III replication in cell culture", 1986; Biochem. Pharmacol. 35:4110–4113.

Shipley, et al., "Recent X–ray Diffraction Studies of Biological Membranes and Membrane Components", in: *Biomembranes*, 1973; vol. 2:1.

Stevens, et al., "In vitro Antiherpetic Activity of Water––Soluble Amphotericin V Methyl Ester", 1975; Arc Virol. 48:391–394.

Szoka, et al., "Comparative Properties and Methods of Preparation of Lipid Vesicles (Liposomes)[1]", 1980; Ann. Rev. Biophys. Bioeng. 9:467–508.

Taylor, et al., "Amphotericin B in Liposomes: A Novel Therapy for Histoplasmosis", 1982; Am. Rev. Respir. Dis. 125:610–611.

Tremblay, et al., "Efficacy of Liposome–Intercalated Amphotericin B in the Treatment of Systemic Candidiasis in Mice", 1984; Antimicrob. Agents Chemo. 26:170–173.

U.S. Appl. No. 08/405,623, filing date Sep. 12, 1989, Janoff et al., pending.

U.S. Appl. No. 08/844,248, filing date Mar. 24, 1986, Janoff et al., pending.

U.S. Appl. No. 08/604,503, filing date May 02, 1984, Janoff et al., abandoned.

U.S. Appl. No. 08/498,268, filing date May 26, 1983, Janoff et al., abandoned.

U.S. Appl. No. 08/835,832, filing date Feb. 28, 1986, Fountain et al., pending.

U.S. Appl. No. 08/225,327, filing date Jul. 28, 1988, Lenk et al., pending.

U.S. Appl. No. 08/079,309, filing date Jul. 29, 1987, Lenk et al., abandoned.

U.S. Appl. No. 08/136,267, filing date Dec. 22, 1987, Madden et al., pending.

U.S. Appl. No. 08/360,964, filing date Jun. 26, 1989, Janoff et al., pending.

U.S. Appl. No. 08/284,751, filing date Dec. 12, 1988, Bally et al., pending.

U.S. Appl. No. 08/759,419, filing date Jul. 26, 1985, Janoff et al., pending.

U.S. Appl. No. 08/749,161, filing date Jun. 26, 1985, Bally et al., abandoned.

U.S. Appl. No. 08/638,809, filing date Aug. 08, 1984, Janoff et al., abandoned.

Klimchak, et al., "Scale–up of liposome products, Biopharm. Manufacturing", vo., 1, No. 2, Feb. 1988, pp. 18–21.

Venkataram, et al., "Characteristics of Drug–Phospholipid Coprecipitates I: Physical Properties and Dissolution Behavior of Griseofulvin–Dimyristoylphosphatidylcholine Systems", J. Pharm Sci, 73(6):757–761, 1984.

LOW TOXICITY DRUG-LIPID SYSTEMS

CORRESPONDING U.S. PATENT APPLICATIONS

This application is a continuation of Ser. No. 07/876,121 filed Apr. 29, 1992, now abandoned, which is a continuation of Ser. No. 07/236,700 filed Aug. 25, 1988, now abandoned, which is a continuation-in-part of Ser. No. 07/136,267 filed Dec. 22, 1987, now U.S. Pat. No. 4,963,297; and a continuation-in-part of Ser. No. 164,580 filed Mar. 7, 1988, now abandoned, which is a continuation-in-part of Ser. No. 07/069,908 filed Jul. 6, 1987, now abandoned, which is a continuation-in-part of Ser. No. 07/022,157 filed Mar. 5, 1987, now abandoned; and a continuation-in-part of Ser. No. 07/225,327 filed Jul. 28, 1988, now abandoned, which is a continuation of Ser. No. 07/079,309, filed Jul. 29, 1987, now abandoned.

BACKGROUND OF THE INVENTION

The present invention is directed to formulations and methods for making drug-associated lipid complexes at high drug:lipid ratios (high drug:lipid complexes, or HDLCs). Such formulations are generally substantially equivalent or greater in efficacy to the same drug in their free form, yet have lower toxicity. Additionally, methods for the formation of such HDLCs are disclosed. More particularly, the invention is directed to the use of these high drug:lipid complexes with the toxic antifungal polyene antibiotics, specifically, amphotericin B and nystatin.

The high drug:lipid complexes (HDLCs) of the present invention can be made by techniques substantially the same as those for making liposomes. The invention includes the use of these HDLC structures in association with bioactive agents such as drugs, specifically the polyene antibiotics such as amphotericin B and nystatin.

As another aspect of the invention, a novel method for forming liposomes (or HDLCs) without the use of organic solvents is disclosed. Entrapment or association of a drug into the liposomes proceeds via an ethanol or an aqueous intermediate.

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

The original liposome preparation of Bangham et al. (J. Mol. Biol., 1965, 13:238–252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (Biochem. Biophys. Acta., 1967, 135:624–638), and large unilamellar vesicles.

Techniques for producing large unilamellar vesicles (LUVs), such as, reverse phase evaporation, infusion procedures, and detergent dilution, can be used to produce liposomes. A review of these and other methods for producing liposomes may be found in in the text Liposomes, Marc Ostro, ed., Marcel Dekker, Inc., New York, 1983, Chapter 1, the pertinent portions of which are incorporated herein by reference. See also Szoka, Jr. et al., (1980, Ann. Rev. Biophys. Bioeng., 9:467), the pertinent portions of which are also incorporated herein by reference. A particularly preferred method for forming LUVs is described in Cullis et al., PCT Publication No. 87/00238, Jan. 16, 1986, entitled "Extrusion Technique for Producing Unilamellar Vesicles" incorporated herein by reference. Vesicles made by this technique, called LUVETS, are extruded under pressure through a membrane filter. Vesicles may also be made by an extrusion technique through a 200 nm filter; such vesicles are known as $VET_{200}$s. These vesicles may be exposed to at least one freeze and thaw cycle prior to the extrusion technique; this procedure is described in Mayer et al., 1985, Biochem. et. Biophys. Acta., 817:193–196, entitled "Solute Distributions and Trapping Efficiencies Observed in Freeze-Thawed Multilamellar Vesicles," relevant portions of which are incorporated herein by reference.

In the practice of this invention, a class of liposomes and method for their formation, characterized as having substantially equal lamellar solute distribution is preferred. This preferred class of liposomes is denominated as stable plurilamellar vesicles (SPLV) as defined in U.S. Pat. No. 4,522,803 to Lenk et al. and includes monophasic vesicles as described in U.S. Pat. No. 4,588,578 to Fountain et al. and frozen and thawed multilamellar vesicles (FATMLV) as described above.

A variety of sterols and their water soluble derivatives have been used to form liposomes; see specifically Janoff et al., U.S. Pat. No. 4,721,612, issued Jan. 26, 1988, entitled "Steroidal Liposomes". Mayhew et al., PCT Publication No. WO 85/00968, published Mar. 14, 1985, describe a method for reducing the toxicity of drugs by encapsulating them in liposomes comprising alpha-tocopherol and certain derivatives thereof. Also, a variety of tocopherols and their water soluble derivatives have been used to form liposomes; see Janoff et al., PCT Publication No. 87/02219, published Apr. 23, 1987, entitled "Alpha Tocopherol-Based Vesicles" and incorporated herein by reference.

In a liposome-drug delivery system, the bioactive agent such as a drug is entrapped in the liposome and then administered to the patient to be treated. For example, See U.S. Pat. Nos. 3,993,754 to Rahman; 4,145,410 to Sears; 4,235,871 to Papahadjopoulos; 4,224,179 to Schneider; 4,522,803 to Lenk; and 4,588,578 to Fountain. Alternatively, if the drug is lipophilic, it may associate with the lipid bilayer. In the present invention, the terms "entrap" or "encapsulate" shall be taken to include both the drug in the aqueous volume of the liposome as well as drug associated with the lipid bilayer.

Many drugs that are useful for treating disease show toxicities in the patient; such toxicities may be cardiotoxicity, as with the antitumor drug doxorubicin, or nephrotoxicity, as with the aminoglycoside or polyene antibiotics such as amphotericin B. Amphotericin B is an extremely toxic antifungal polyene antibiotic, but the single most reliability in the treatment of life-threatening fungal infections (Taylor et al., Am. Rev. Respir. Dis., 1982, 125:610–611). Because amphotericin B is a hydrophobic drug, it is insoluble in aqueous solution and is commercially available as a colloidal dispersion in desoxycholate, a detergent used to suspend it which in itself is toxic. Amphotericin B methyl ester and amphotericin B have also been shown to be active against the HTLV-III/LAV virus, a lipid-enveloped retrovirus, shown in the etiology of acquired immuno-deficiency syndrome (AIDS) (Schaffner et al., Biochem, Pharmacol., 1986, 35:4110–4113). In this study, amphotericin B methyl ester ascorbic acid salt (water soluble) and amphotericin B were added to separate cultures of HTLV-III/LAV infected cells and the cells assayed for replication of the virus. Results showed that amphotericin B methyl ester and amphotericin B protected target cells against the cytopathic effects of the virus, similar to that demonstrated for the herpes virus (Stevens et al., Arch. Virol., 1975, 48:391).

Reports of the use of liposome-encapsulated amphotericin B have appeared in the literature. Juliano et al. (Annals N.Y. Acad. Sci., 1985, 446:390–402) discuss the treatment of systemic fungal infections with liposomal amphotericin B. Such liposomes comprise phospholipid, for example dimyristoylphosphatidylcholine (DMPC) and dimyristoylphosphatidylglycerol (DMPG) in a 7:3 mole ratio, and cholesterol. Acute toxicity studies ($LD_{50}$s) and in vitro assays comparing free and liposome-entrapped amphotericin B showed lower toxicities using the liposomal preparations with substantially unchanged antifungal potency. Lopez-Berestein et al. (J. Infect. Dis., 1986, 151:704–710) administered liposome-encapsulated amphotericin B to patients with systemic fungal infections. The liposomes comprised a 7:3 mole ratio of DMPC:DMPG, and the drug was encapsulated at a greater than 90% efficiency. As a result of the liposomal-drug treatment at 5 mol % amphotericin B, 66% of the patients treated responded favorably, with either partial or complete remission of the fungal infection. Lopez-Berestein et al. (J. Infect. Dis., 1983, 147:939–945), Ahrens et al., (S. Jour. Med. Vet. Mycol., 1984, 22:161–166), Panosian et al. (Antimicrob. Agents Chemo., 1984, 25:655–656), and Tremblay et al. (Antimicrob. Agents Chemo., 1984, 26:170–173) also tested the comparative efficacy of free versus liposomal amphotericin B in the treatment and prophylaxis of systemic candidiasis and leishmaniasis (Panosian et al., supra.) in mice. They found an increased therapeutic index with the liposome-encapsulated amphotericin B in the treatment of candidiasis. In all cases, it was found that much higher dosages of amphotericin B may be tolerated when this drug is encapsulated in liposomes. The amphotericin B-liposome formulations had little to no effect in the treatment of leishmaniasis.

Proliposomes (lipid and drug coated onto a soluble carrier to form a granular material) comprising DMPC:DMPG, ergosterol, and amphotericin B have also been made (Payne et al., J. Pharm. Sci., 1986, 75:330–333).

In other studies, intravenous treatment of cryptococcosis in mice with liposomal amphotericin B was compared to similar treatment with amphotericin B-desoxycholate (Graybill et al., J. Infect. Dis., 1982, 145:748–752). Mice treated with liposomal-amphotericin B showed higher survival times, lower tissue counts of cryptococci, and reduced acute toxicity. Multilameller liposomes used in this study contained ergosterol. Taylor et al. (Am. Rev. Resp. Dis., 1982, 125:610–611) treated histoplasmosis in mice with liposomal-amphotericin B wherein the liposomes contained ergosterol and phospholipids. The liposomal preparations were less toxic, more effective in treating histoplasmosis, and had altered serum and tissue distributions, with lower serum levels and higher liver and spleen concentrations than that of the free amphotericin B preparations.

In the above-mentioned studies, lipid-containing liposomes were used to ameliorate the toxicity of the entrapped drug, with the trend towards increasing the lipid content in the formulations in order to buffer drug toxicity. Applicants have surprisingly found that in fact a low lipid constituent decreases the toxicity most efficiently. In the formation of the HDLCs of the invention by an MLV method, a mixed population of HDLCs with MLVs can result; these preparations are those employing from about 6 to about 25 mole percent of drug (amphotericin B), with the proportion of HDLCs increasing as the mole percent drug increases. Preparations employing 25 mole percent to about 50 mole percent of drug are substantially HDLCs, free of liposomes. Alternatively, preparations containing 5 mole percent hydrophobic drug and less are substantially liposomal with some HDLCs. The separation of HDLCs from heterogenous populations if necessary, can be performed using any separation technique known in the art, for example, density gradient centrifugation.

The processes used to form these HDLCs can be substantially the same as those used to form liposomes, but in the present invention using high drug:lipid ratios, more HDLCs than liposomes are formed with unexpectedly large reduction in toxicity, compared to the liposomal formulations.

SUMMARY OF THE INVENTION

The present invention discloses HDLC (high drug:lipid ratio complexes) systems which comprise lipids and bioactive agents including drugs. Such HDLCs may comprise phospholipids such as DMPC and DMPG, preferably in a 7:3 mole ratio or saturated phospholipids or fatty acid phospholipids. The bioactive agent is preferably a drug, such as an antifungal drug such as nystatin or amphotericin B. The mole percent of the drug present is preferably from about 6 to about 50 mole percent, preferably 30 to 50 mole percent. Pharmaceutical compositions of the HDLCs, preferably comprising a drug such as amphotericin B, are made comprising pharmaceutical acceptable carriers or diluents, and these compositions may be administered parenterally. Such compositions are used to treat infectious diseases such as fungal infections, by administering them to mammals such as humans. The HDLC-containing compositions of the present invention include those compositions substantially free of liposomes and compositions substantially free of liposomes entrapping the drug. The term "substantially free" shall be taken to mean generally no more than about 10 percent by weight of liposomes, preferably no more than about 5%, and more preferably no more than about 3%.

Various methods for preparing the HDLCs of the invention are disclosed; for example, techniques that first solubilize the drug, specifically amphotericin B in a solvent such as DMSO or methanol The lipid (preferably DMPC:DMPG in a 7:3 mole ratio) is solubilized in a solvent such as methylene chloride, and the lipid and drug solutions mixed. The solvents may be evaporated under reduced pressure, resulting in a thin lipid-drug film. The film may be hydrated in an aqueous solution such as saline, PBS, or glycine buffer, forming HDLCs. Alternatively, the aqueous solution may be added to the solvent-containing drug and lipid phase prior to evaporation of the solvent. As another alternative, the resulting dry lipid-drug film may be resuspended in a solvent, such as methylene chloride and again evaporated under reduced pressure prior to hydrating the film. A dehydration procedure may also be used; in this process a dry lipid-drug film is dehydrated to form a flake which is hydrated with aqueous solution.

In an alternative method for forming the HDLCs of the invention, lipid particles (or liposomes) containing bioactive agent (drug, for example polyene antifungals such as amphotericin B) made by the MLV process containing about 6 percent to 50 mole percent amphotericin B are formed and then the particles (or liposomes) are subjected to a heating cycle, at about 25° C. to about 60° C., most preferably about 60° C. Such a cycle forms a more highly ordered and less toxic amphotericin B/lipid complex.

In another aspect of the invention, an absorbance spectrum technique is used to determine the toxicity of a drug (e.g. a polyene antifungal such as amphotericin B)-lipid complex. The absorbance spectrum of a drug is specific for that drug; the signature of the drug may be a peak or series of peaks in the ultraviolet or the visible range. The signature peak for amphotericin B, (appearing in FIG. 12, dissolved in deoxycholate), is between 300 and 500 nm, and has characteristic peaks, the most representative of these peaks being the one arising at 413 nm. The attenuation of this peak by complexing the drug with lipid can be used quantitatively as a measure of toxicity of the HDLC. In other words, the degree of toxicity may be determined by the intensity of the absorbance peak height.

A liposome-loading process is also disclosed wherein the drug, specifically the polyene antibiotic amphotericin B is dispersed by sonication in a solvent such as ethanol to which has been added an acid such as hydrochloric acid. A lipid film, specifically comprising DMPC:DMPG in an about 7:3 mole ratio, is hydrated with an aqueous solution, specifically aqueous buffer such as PBS, and an aliquot of the acidified ethanol solution containing the drug is loaded into the liposomes by adding it to the liposome preparation. The ethanol in the resulting suspension is removed and the solution is resuspended with an aqueous solution. Depending on the mole ratio of drug co-mixed with the lipid, the process favors formation of HDLCs rather than liposomes; e.g. at mole percent of drug of about 16 and above, more HDLCs are formed than liposomes. Alternatively, at 0–15 mole percent drug, the process favors formation of liposomes. Liposomes or HDLCs made by this acidified ethanol loading process may be prepared for use as pharmaceutical compositions by the addition of pharmaceutically acceptable carriers or diluent, and may be used in the treatment of fungal infections by administering them to a mammal such as a human.

DETAILED DESCRIPTION OF THE INVENTION

Figure 1:
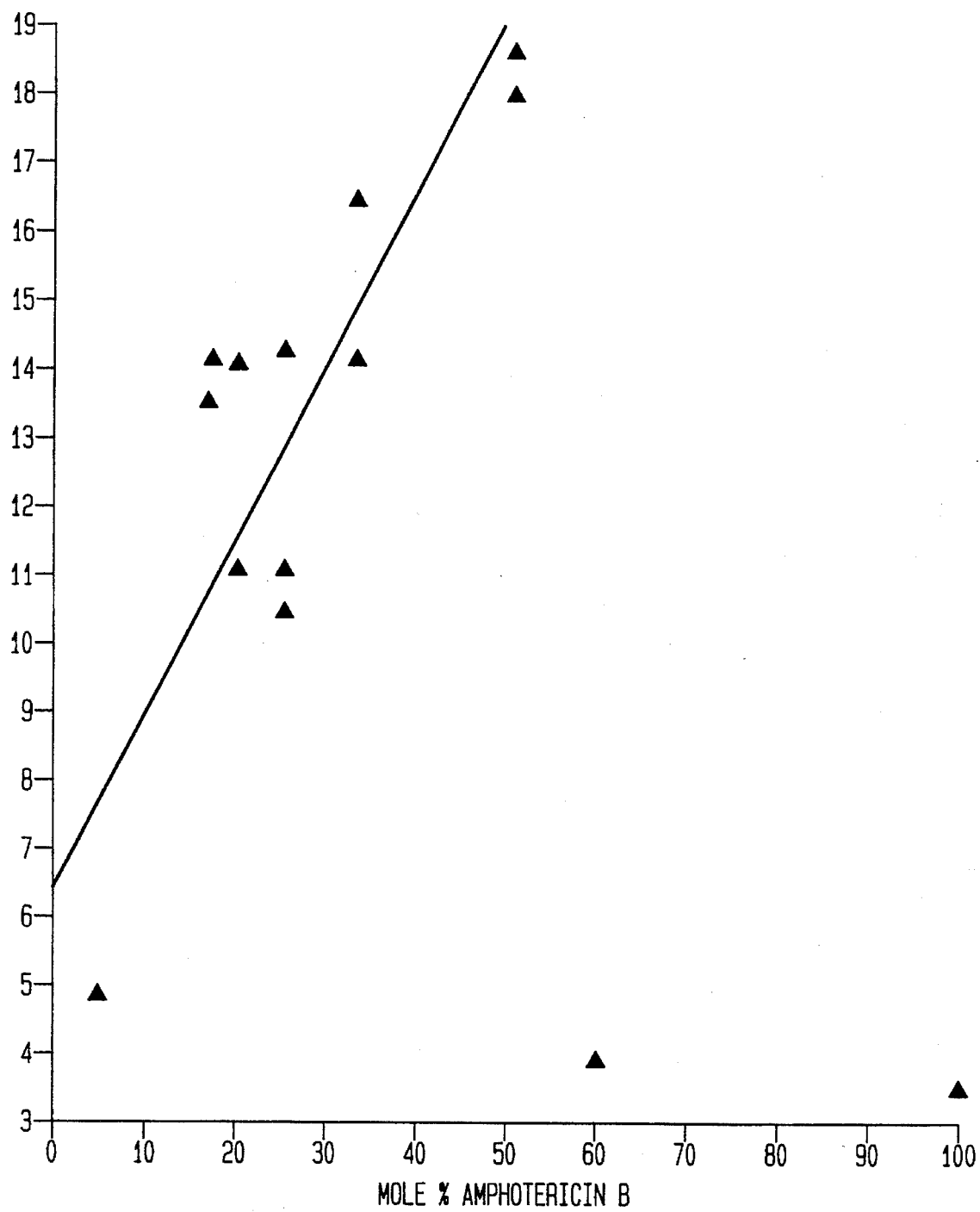
FIG. 1 is a graph depicting acute toxicity measured by $LD_{50}$ as a function of mole percent of amphotericin B in the preparation.

Nonliposomal high drug:lipid ratio complexes (HDLCs) having unique properties, and methods for their preparation are described. These HDLCs contain a bioactive agent such as a hydrophobic drug, which, when the HDLC is administered to an organism can have substantially equivalent or greater efficacy and lower toxicity as compared to the drug administered in either free or liposomal form. Such HDLCs comprise a high drug:lipid mole ratio (greater than about 5 mol % drug). The present invention surprisingly demonstrates the decreased toxicity of complexes containing less lipid, such as the instant HDLC systems, as compared to liposomal systems. The invention involves HDLC formulations for use as drug carrier systems in association with drugs such as the anti-fungal polyene antibiotics amphotericin B and nystatin. Such formulations, unlike the current commercially available formulations, are stable in aqueous solutions such as saline.

Additionally, a new liposome-loading method is described which loads liposomes by entrapping a drug via a solvent intermediate. This solvent has the characteristics that it solubilizes the bioactive agent, such as amphotericin B, it does not disrupt the liposome membrane structure, and it is compatible with an aqueous solution such as water. Such a solvent is ethanol. This method proceeds without the use of organic solvents. Depending upon the mole percent of drug used in the preparation, HDLCs rather than liposomes will be formed. In the case where the formation of HDLCs are favored, the process loads the HDLCs with drug.

HDLCs refer to drug-associated lipid in particulate form, such particulates being nonliposomal in nature. When formed using an MLV process, such HDLCs are characterized, for example, by: (1) freeze-fracture electron micrographs (Deamer et al., Biochim. Biophys. Acta, 1970, 219:47–60), demonstrating nonliposomal complexes; (2) captured volume measurements (Deamer et al., Chem. Phys. Lipids, 1986, 40:167–188), demonstrating essentially zero entrapped volumes and therefore being nonliposomal; (3) differential scanning calorimetry (DSC) (Chapman, D., in: Liposome Technology, Gregoriadis, G., ed., 1984, CRC Press, Boca Raton), showing no lipid bilayer pre-transition phase or main transition; (4) $^{31}$P-NMR spectra (Cullis et al., 1982 in: Membrane Fluidity in Biology, Academic Press, Inc., London & N.Y.), suggesting characteristics of highly immobilized lipid (broad isotropic); and (5) x-ray diffraction data (Shipley et al., in: Biomembranes, 1973, Chapman, D. and Wallach, D., eds., Vol 2:1, Academic Press, Inc., London & N.Y.), indicative of gel phase lipid. Also characteristic of these systems is the complete association of the drug with the lipid as evidenced by density gradient centrifugation. In this technique the gradient is centrifuged at an elevated force (about 230,000×g) for about 24 hours. This insures that all the components in the gradient reach their equilibrium density positions. Elution profiles of these systems show overlapping drug and lipid peaks, which indicates all of the drug is associated with the lipid.

One aspect of the present invention is a drug:lipid ratio that forms HDLCs which results in substantially equivalent or greater efficacy of the drug while generally decreasing acute toxicity as measured by $LD_{50}$ in mice (FIG. 1). Applicants have found that between about a 6 and 50 mole percent of hydrophobic drug meets such requirements, with a preferred ratio being between about 15 and 50, more preferably between about 25 and 50, most preferably about 25 and 45 mole percent hydrophobic drug. Where drug concentrations exceed about 6 mole percent and approach 25 mole %, mixed populations of liposomes and HDLCs are formed. Within this range, as the mole percent of drug approaches 25, a greater percent of the structures are HDLC rather than liposomes. At drug concentrations of about 5 mole percent and less, and to a lower limit of lipid known to those in the art as the "critical micelle concentration", mixed HDLC/liposome populations, but substantially liposomal structures, are present. Such liposomes may be formed by the novel ethanol intermediate process of the present invention.

Characteristic of the above-mentioned HDLCs are various drug-lipid dispersions observed upon density centrifugation. Separations of the drug-lipid (DMPC:DMPG at a 7:3 mole ratio) complex on the isopycnic sucrose density columns showing banding that is dependent on the drug:lipid ratio and the method of preparation. In systems comprising 5 mole percent drug made by the MLV process, two major bands of material are observed; one of liposomes and one where drug is associated with the lipid (HDLCs). Preparations containing 25 and 50 mole percent drug showed a single band wherein most of the drug is associated with the lipid. Surprisingly, these low-lipid/higher mole percent drug systems were less toxic. FIG. 1 shows $LD_{50}s$(mg/kg) in mice as a function of the mole percent of the drug amphotericin B in the preparation. The $LD_{50}$s increase between 5 and 50 mole percent drug, then drop off at 60 mole percent. Also plot is the $LD_{50}$ for the commercially available form of this drug; Fungizone, at about 3.5 mg/kg. In vitro blood cell lysis (hemolysis) demonstrates the same toxicity phenomenon.

Captured volume studies (entrapment of solute (in ul) per umol lipid) performed on MLV preparations of drug-lipid associations at varying mole percent drug demonstrate the unusual nature of the 25 mole percent and greater (HDLC) formulations; these systems entrap no solute and therefore are not liposomal. Freeze fracture electron micrographs of these same systems demonstrate liposomes at 0 and 5 mole percent drug, but nonliposomal HDLCs at 25 and 50 mole percent drug.

Figure 2:
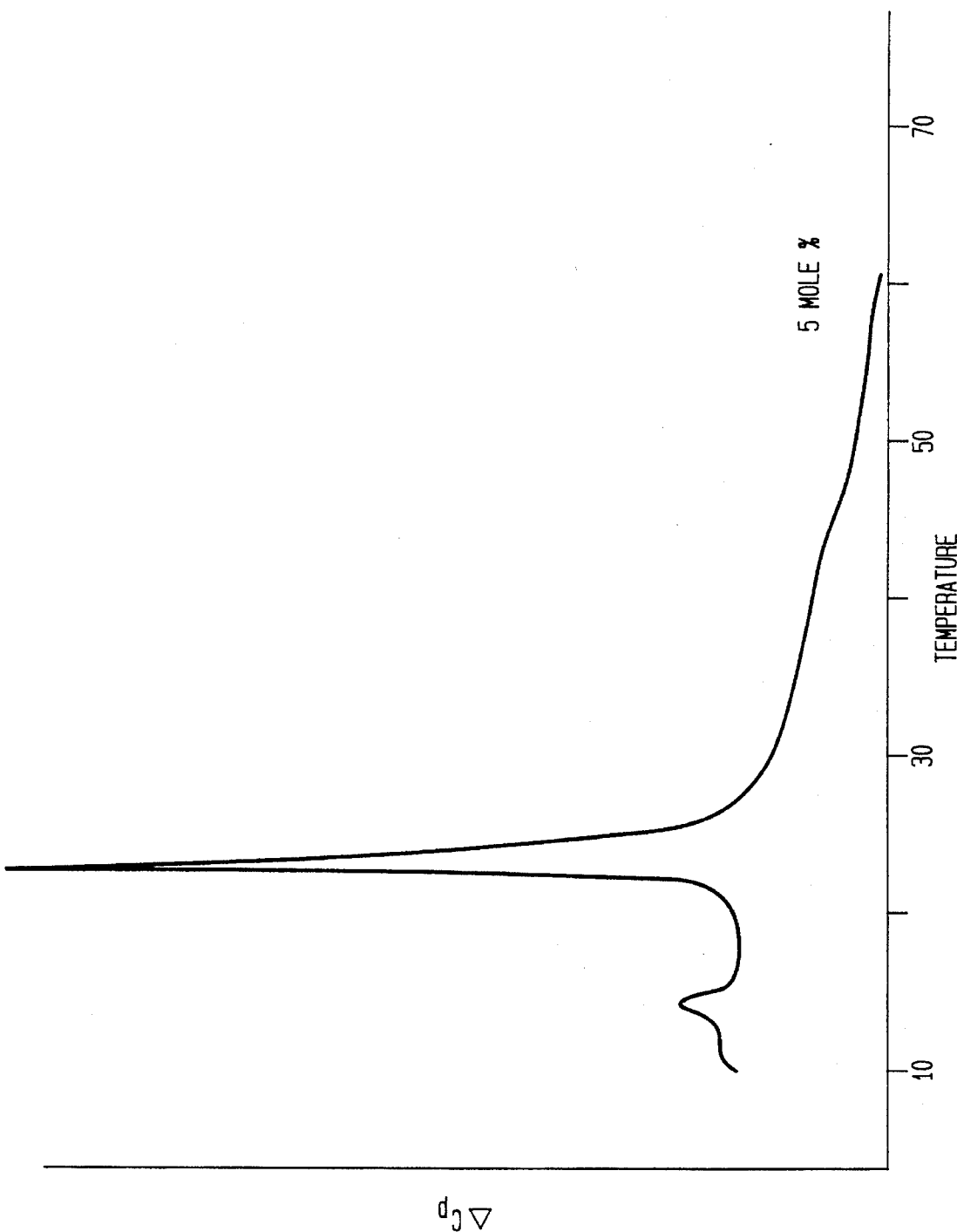
FIG. 2 is a differential scanning calorimetry spectrum of a liposomal (MLV) preparation containing 5 mole percent amphotericin B.
Figure 3:
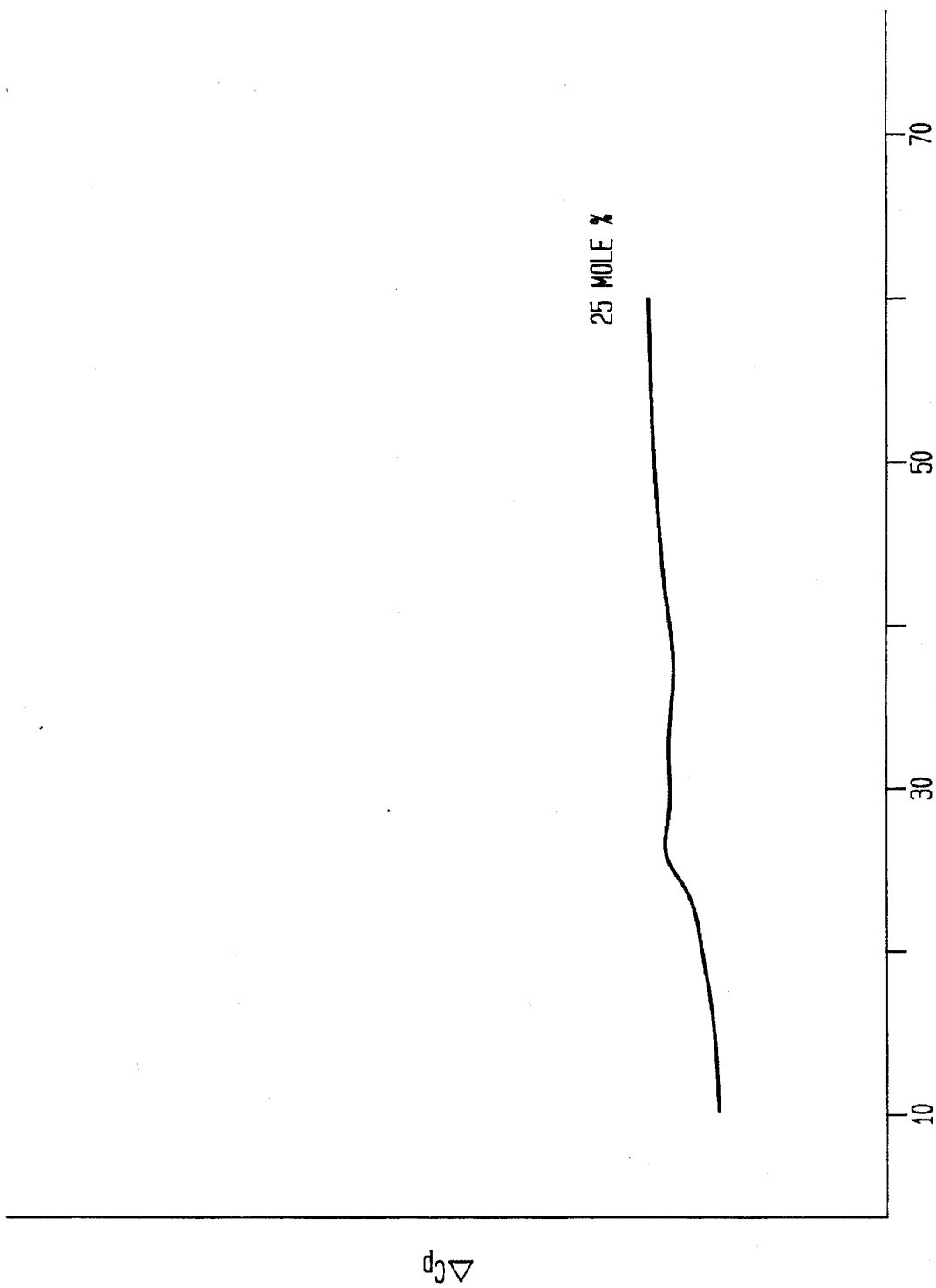
FIG. 3 is a differential scanning calorimetry spectrum of an HDLC preparation (MLV process) containing 25 mole percent amphotericin B.
Figure 4:
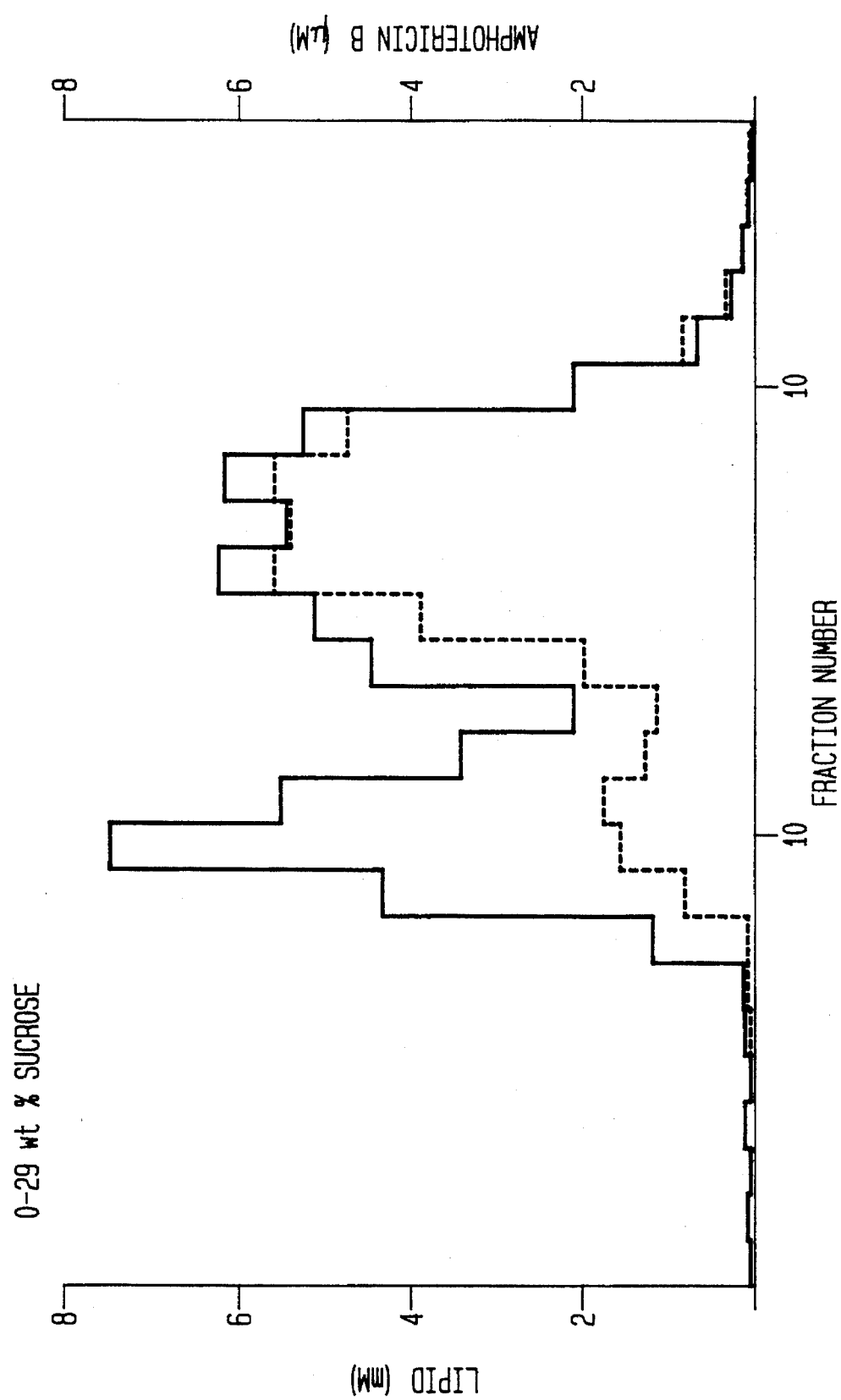
FIG. 4 is a graph of an isopycnic gradient of multilamellar liposomes containing 5 mole percent amphotericin B. Lipid (solid line); amphotericin B (broken line).
Figure 5:
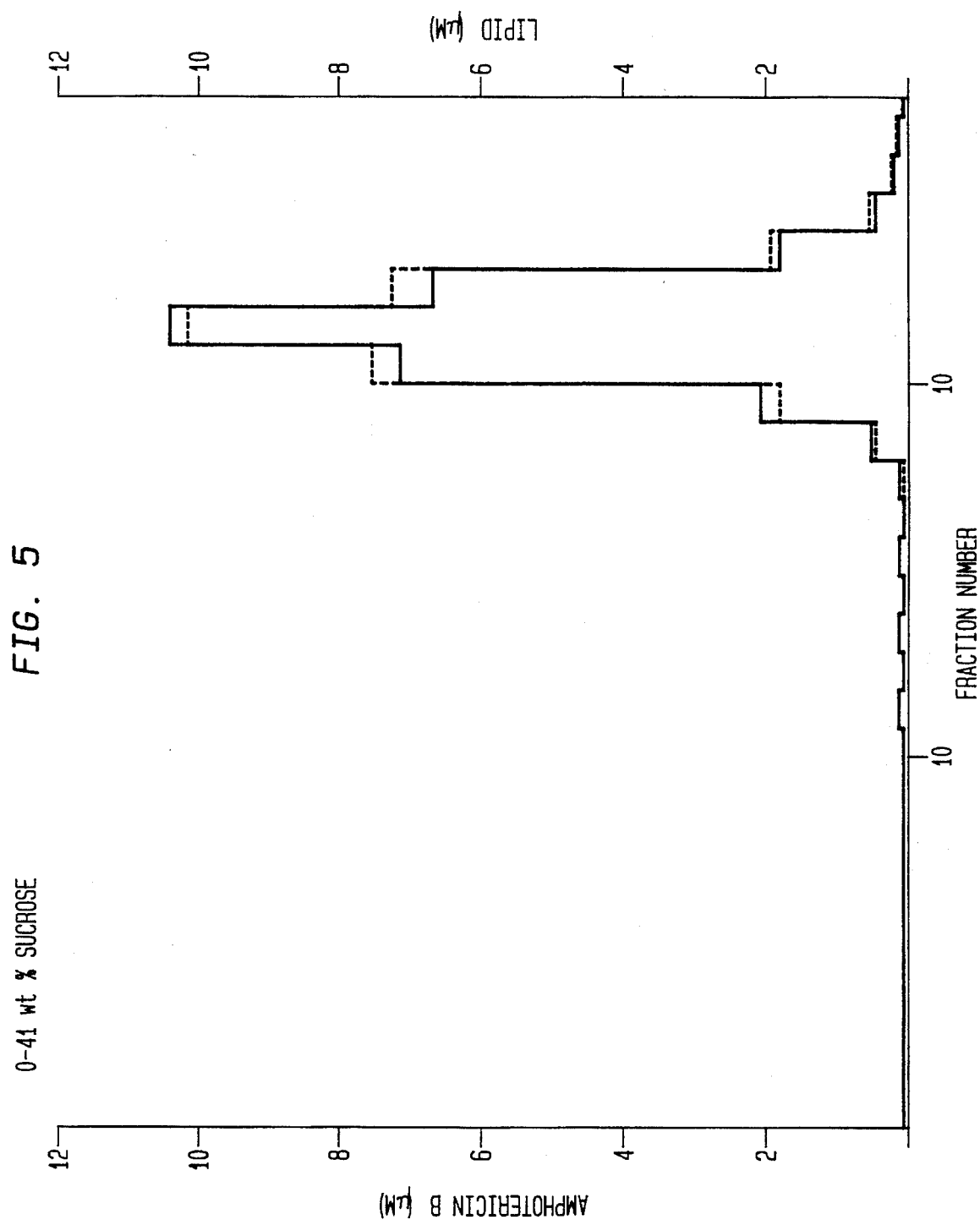
FIG. 5 is a graph of an isopycnic gradient of HDLCs (MLV process) made with 50 mole percent amphotericin B. Lipid (solid line); amphotericin B (broken line).

Differential scanning calorimetry tracings performed on MLV preparations with varying mole percent drug demonstrate the same phenomena; that is, spectra show transition peaks characteristic of the unperturbed bilayer state lipid at 5 mole percent drug (FIG. 2), but no transition peak at 25 mole percent drug (FIG. 3). In the case of 25 mole percent drug, all the lipid is completely associated with the drug, i.e., the acyl chains of the lipid are not free to undergo a cooperative transition. This data confirms the density centrifugation data which shows a double peak of lipid-associated drug and free lipid at the 5 mole percent drug concentration (FIG. 6), but a single peak where all the lipid is associated with the drug at 25 and 50 mole percent drug concentrations (FIG. 5).

Figure 6:
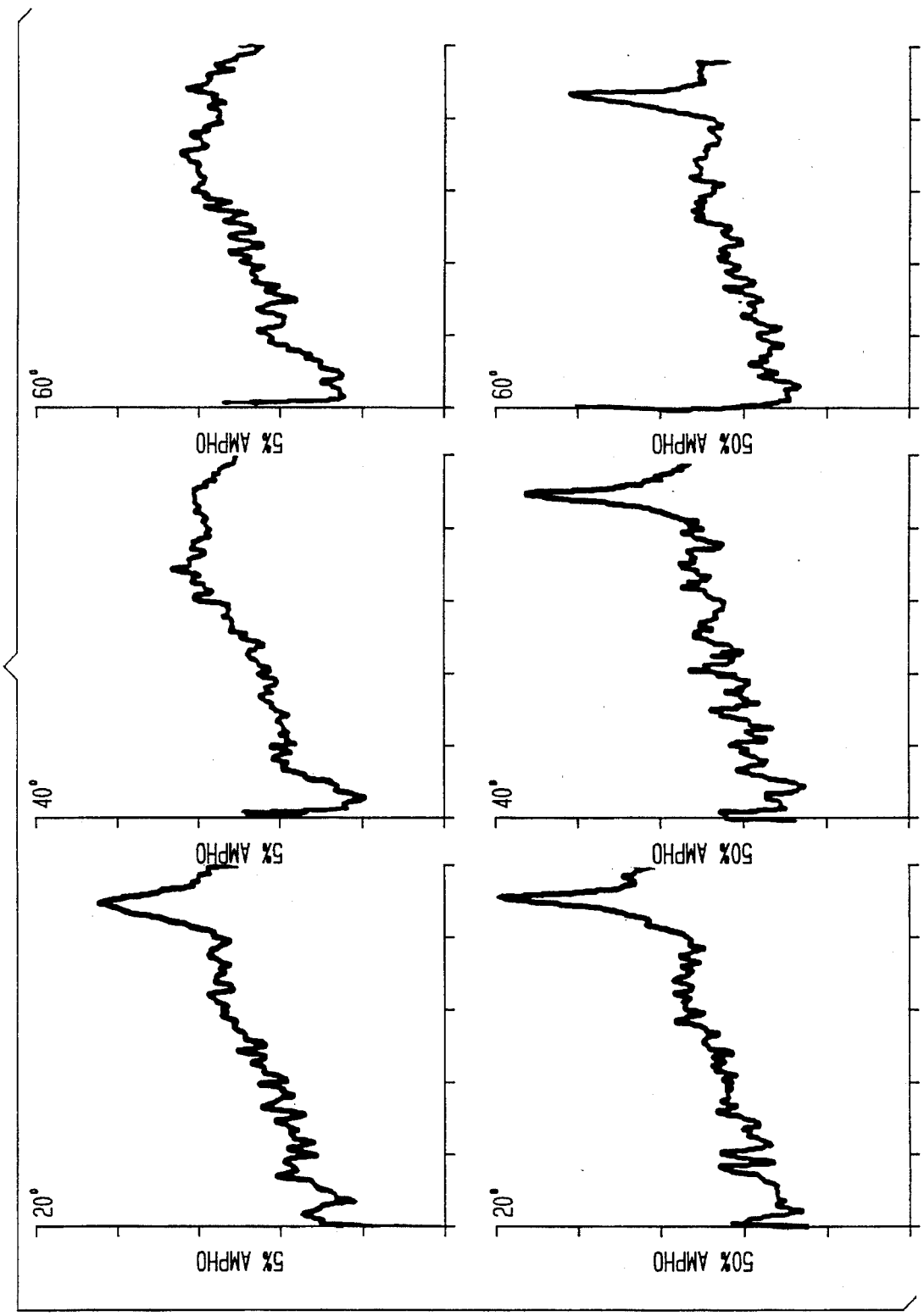
FIG. 6 shows graphs of x-ray diffraction data for liposome and HDLC preparations (MLV process) containing 5 and 50 mole percent (respectively) amphotericin B.
Figure 7:
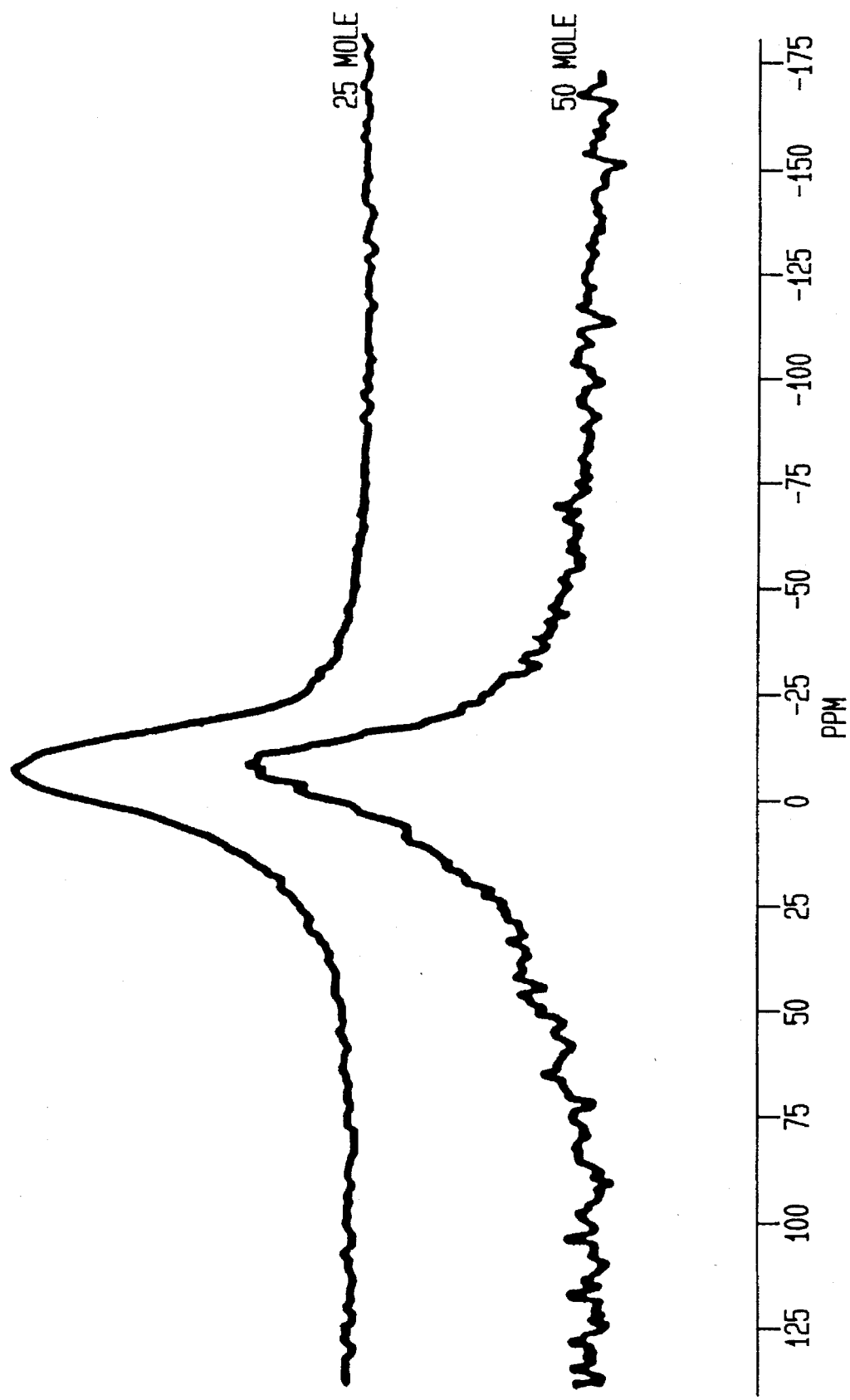
FIG. 7 shows $^{31}$P-NMR spectra for HDLC preparations (MLV process) containing 25 and 50 mole percent amphotericin B.
Figure 8:
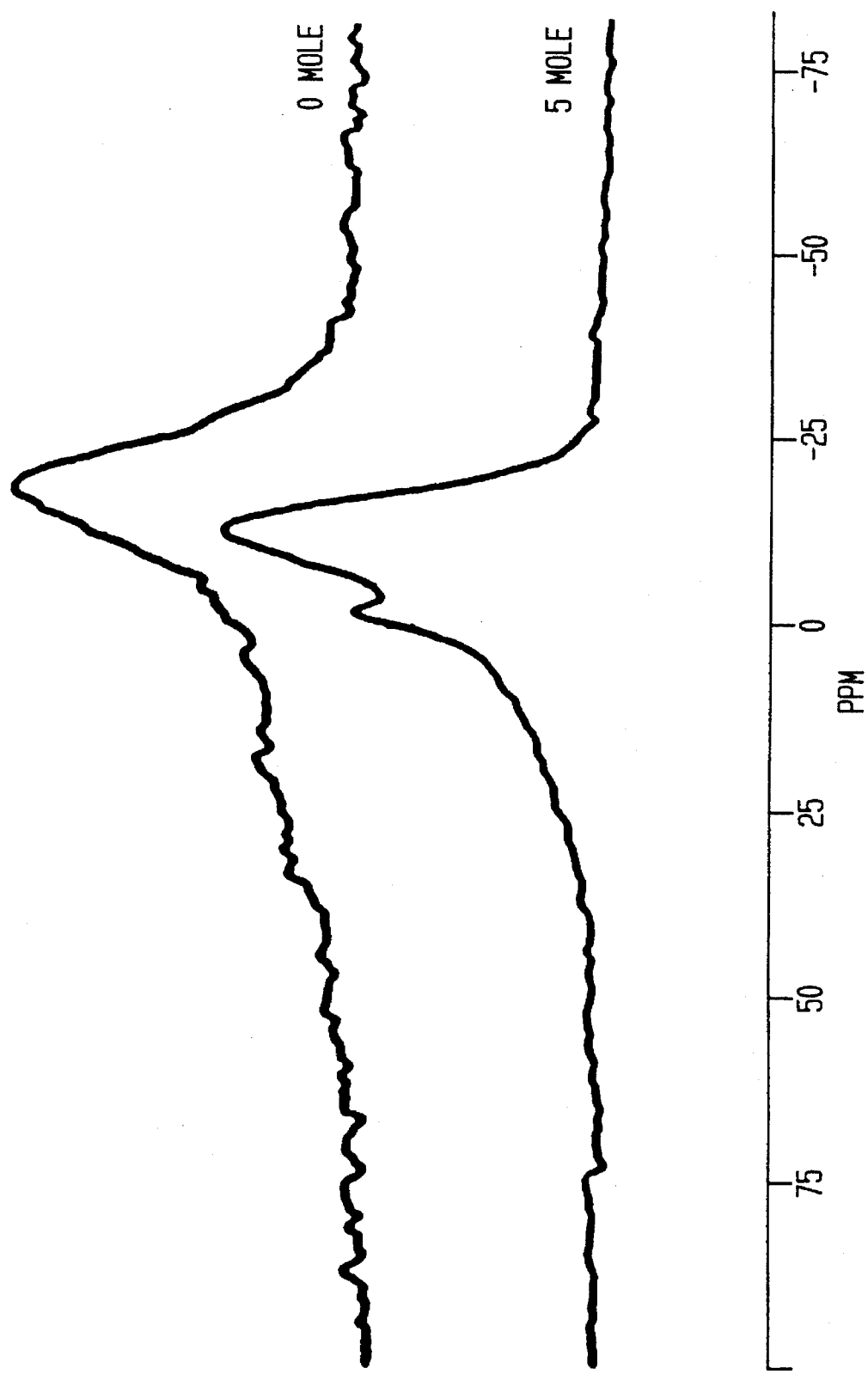
FIG. 8 shows $^{31}$P-NMR spectra for liposome (MLV) preparations containing 0 and 5 mole percent amphotericin B.
Figure 9:
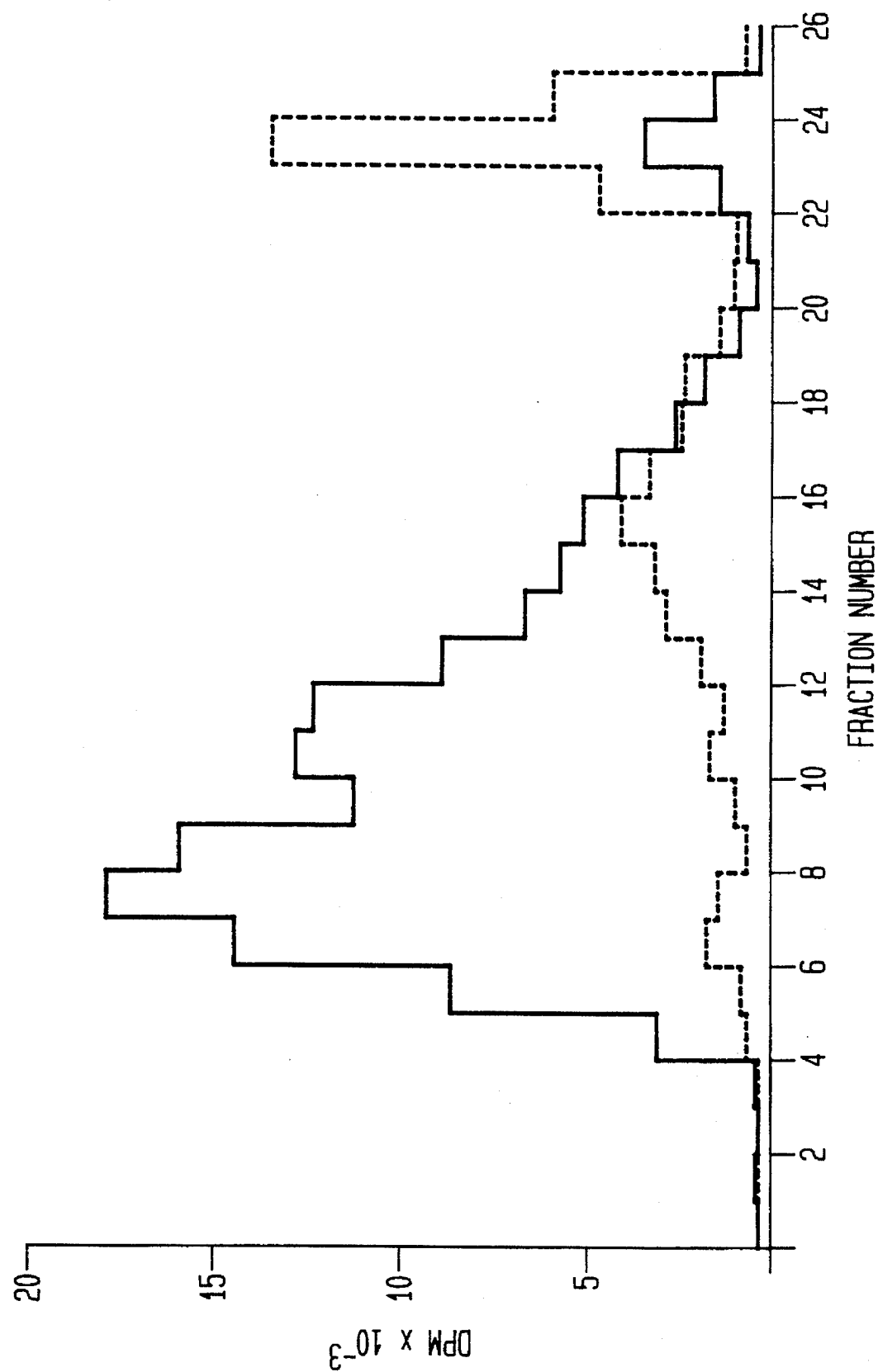
FIG. 9 is a graph of an isopycnic density gradient of amphotericin B-containing liposomes formed by the acidified ethanol process containing 5 mole percent amphotericin B. Lipid (solid line); amphotericin B (broken line).

X-ray data at 5 mole percent (MLV process) shows gel phase lipid at low temperatures, with a transition to liquid crystalline phase at the characteristic temperature of 23° C. At 50 mole percent drug, however, the lipid is in the gel phase at all temperatures; there is no transition due to all the lipid being in tight association with the drug (FIG. 6). Similar data for $^{31}$P-NMR studies show the lack of the free lipid signal for these higher (25 and 50) mole percent drug formulations (HDLCs); the low field shoulder/high field peak characteristics of this type of lipid is absent (FIG. 7), while it is visible in the 0 and 5 mole percent drug samples (FIG. 8).

Although lipid complex systems with their associated high drug-lipid ratios are one aspect of the present invention, liposome-forming procedures may be used in the formation of these lipid complexes. Specifically, these procedures include those that form liposomes known as multilamellar vesicles (MLV). Other processes that may be used are those that form stable plurilamellar vesicles (SPLV), large unilamellar vesicles formed by an extrusion procedure (LUVETS), or other liposome-forming procedures known in the art. The process for forming SPLVs is disclosed in Lenk et al., U.S. Pat. No. 4,522,803, issue Jun. 11, 1985, and the LUVET procedure disclosed in Cullis et al., PCT Application No. WO 86/00238, published Jan. 16, 1986; relevant portions of each are incorporated herein by reference. In the novel liposome formation aspect of the present invention, liposomes are formed in aqueous solution to which is added the drug to be entrapped, in acidified ethanol. In another liposome forming embodiment of the present invention, amphotericin B is incorporated into liposomes via an aqueous intermediate. In this technique, amphotericin B is suspended in an aqueous solution, for example distilled water, by sonication. The suspended drug is then admixed with a suspension of lipid in aqueous solution, such as distilled water or sodium chloride solution. The mixture is incubated at or above the transition temperature of the lipid employed, with the resultant formation of MLVs.

The lipids which can be (1) employed in making the lipid complexes, and (2) used in the novel liposome formation technique of the present invention, are the phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination. Saturated phospholipids such as hydrogenated soy PC may also be used. The phospholipids can be synthetic or derived from natural sources such as egg or soy. In the preferred embodiments, the phospholipids dimyristoylphosphatidylcholine (DMPC) and dimyristoylphosphatidylglycerol (DMPC) are used in combination in any mole ratio, from about 99:1 to about 1:99 DMPC:DMPG, preferably in about a 7:3 mole ratio. DMPC and dimyristoylphosphatidylserine (DMPS) may also be used in combination. However, DMPC alone may be used. The lipid complexes and liposomes can also contain asteroid component as part of the lipid phase, such steroids may be cholesterol, polyethylene glycol derivatives of cholesterol (PEC-cholesterols), coprostanol, cholestanol, cholestane, organic acid derivatives of sterols such as cholesterol hemisuccinate (CHS), and the like. Further lipid complex-forming compositions are fatty acids such as myristic acid, isopropyl myristate, isostearic acid, sucrose disrestate, propylene glycol monostearate, and cetylated monoglyceride. Other substances that can be employed include lipids such as trimyristin, the fatty alcohols such as cetyl alcohol and myristyl alcohol, and fatty esters such as myristic acid ethyl ester.

Organic acid derivatives of tocopherols may also be used as complex- or liposome-forming ingredients, such as alpha-tocopherol hemisuccinate (THS). Both CHS- and THS-containing complexes and their tris salt forms may generally be prepared by any method known in the art for preparing liposomes containing these sterols. In particular, see the procedures of Janoff et al., U.S. Pat. No. 4,721,614, issued Jan. 26, 1988, entitled "Steroidal Liposomes", and Janoff et al., PCT Publication No. 87/02219, published Apr. 23, 1987, entitled "Alpha-Tocopherol Based Vesicles," filed Sep. 24, 1986, respectively, relevant portions of which are incorporated herein by reference.

Bioactive agents such as drugs may be used in the present invention. In the case of HDLCs, bioactive agents used are those that are hydrophobic; in the case of liposomes, the bioactive agents may be either hydrophobic or hydrophilic as liposomes entrap both types of agents. Such bioactive agents include but are not limited to the polyene antibiotics such as the anti-fungal agents pimaricin, candicidin, filipin, and preferably, nystatin and amphotericin B. Other bioactive agents that may be used include but are not limited to antibacterial compounds such as the antibacterial compounds such as the aminoglycosides, for example, gentamicin, antiviral compounds such as rifampacin, anti-parasitic compounds such as antimony derivatives, antineoplastic compounds such as vinblastine, vincristine, mitomycin C, doxorubicin, daunorubicin, methotrexate, and cisplatin, among others, proteins such as albumin, toxins such as diptheria toxin, enzymes such as catalase, hormones such as estrogens, neurotransmitters such as acetylcholine, lipoproteins such as alpha-lipoprotein, glycoproteins such as hyaluronic acid, immunoglobulins such as IgG, immunomodulators such as the interferons or the interleukins, dyes such as Arsenazo III, radiolabels such as $^{14}C$, radio-opaque compounds such as $^{99}Tc$, fluorescent compounds such as carboxy fluorescein, polysaccharides such as glycogen, cell receptor binding molecules such as estrogen receptor protein, nonsteroidal anti-inflammatories such as indomethacin, salicylic acid acetate, ibuprofen, sulindac, piroxicam, and naproxen; anti-inflammatories such as dexamethasone, anti-glaucomic agents such as timolol or pilocarpine, anesthetics such as dibucaine, nucleic acids such as thymine, polynucleotides such as RNA polymers, cardiovascular agents such as alpha-blocker, beta-blocker, calcium channel blockers, AGE inhibitors, and the like, CNS agents and prostaglandins.

During preparation of the HDLCs, as in the general preparation of liposomes, organic solvents may be used. Suitable organic solvents are those with intermediate polarities and dielectric properties (those having a polarity intermediate to opposing electrical charges), which solubilize lipids, and include but are not limited to chloroform, methanol, dimethylsulfoxide (DMSO), methylene chloride, and solvent mixtures such as chloroform:methanol (70:30) and benzene:methanol (70:30). As a result, solutions, defined as mixtures in which the components are uniformly distributed throughout; containing the lipids are formed. Solvents are preferably chosen on the basis of their biocompatibility, low toxicity, and imflammability. When solubilizing the drug, specifically amphotericin B, DMSO is preferred as it is most soluble in DMSO. Methanol may be substituted for DMSO with concomitant increase in solvent volume. For solubilizing lipid, methylene chloride is preferably used due to its low toxicity in humans. In the novel liposome-forming processes of the present invention, ethanol or aqueous solutions are the preferred solvents.

In the hydration step of HDLC formation, aqueous solutions such as distilled water (e.g., USP water for injection), saline, or aqueous buffers may be used. Aqueous buffers that may be used include but are not limited to buffered salines such as phosphate buffered saline ("PBS"), tris-(hydroxymethyl)-aminomethane hydrochloride ("tris") buffers, or glycine buffers at pH of about 7.0 to 7.5, preferably 7.2.

In the formation steps of HDLCs or the novel liposomes, a sonication step may be performed. Such a procedure is performed in a bath sonicator for about 15 to about 30 minutes, at 25° C., at about 50–60 Hz.

The HDLCs or liposomes formed may be sized by extrusion through a filter according to the procedure of Cullis et al., PCT Publication No. 88/00238, published Jan. 16, 1986, relevant portions of which are incorporated herein by reference. Such sizing procedures allow the formation of homogeneous populations of particles, with regard to size. For example, the filtering of the HDLCs may be performed through a tortuous path or a straight through membrane filter, such as a polycarbonate filter.

The HDLCs or liposomes formed by the novel procedures of the present invention may be subject to a lyophilization or dehydration procedure at various stages of formation. For example, the lipid film may be lyophilized after removing the solvent and prior to adding the drug. Alternatively, the lipid-drug film may be lyophilized prior to hydrating the HDLC or liposome. Such dehydration may be carried out by exposing the lipid, HDLC, or liposome to reduced pressure thereby removing all suspending solvent. Alternatively or additionally, the finally hydrated HDLC or liposome preparation may also be dehydrated by placing it in surrounding medium in liquid nitrogen and freezing it prior to the dehydration step. Dehydration with prior freezing may be performed in the presence of one or more protective sugars in the preparation according to the techniques of Bally et al., PCT Publication No. 86/01103 published Feb. 27, 1986, relevant portions of which are hereby incorporated by reference and Schneider et al., U.S. Pat. No. 4,229,360, issued Oct. 21, 1980. Such techniques enhance the long-term storage and stability of the preparations. Other suitable methods, now known or later discovered, may be used in the dehydration of the above-disclosed lipid complex preparations.

One method for formation of the HDLCs of the present invention is an MLV procedure wherein the bioactive agent (e.g., a drug) is dissolved in methanol in a flask to which is then added lipid such as DMPC and DMPG in about a 7:3 mole ratio of DMPC:DMPG, in chloroform. After rotoevaporating the solution at reduced pressure, the dried film is resuspended in PBS and sonicated in a bath sonicator (at about 25° C. for about 30 minutes, about 50–60 Hz) to clarity. At mole ratios of drug:lipid of about 6 and above (to about 60 mole percent), the preparations are nonliposomal HDLC structures substantially free of liposomes. Toxicities of the HDLC preparations are drug:lipid ratio-dependent, preparations of higher drug:lipid ratios (about 16–50 mole percent drug) show less acute toxicity than lower drug:lipid ratio preparations (about 6–15 mole percent drug). As discussed above, preparations containing up to about 5 mole percent drug are substantially liposomal. Another method for the formation of the HDLCs of the invention is wherein the lipid (DMPC:DMPG, 2:1 w/w) is homogenized with an aqueous solution, such as buffer or saline, and admixed with the bioactive agent previously dissolved in an organic solvent such as dimethyl sulfoxide (DMSO). This admixture of the lipid with the bioactive agent (for example, a drug such as amphotericin B) can be by homogenization wherein the bioactive agent solution is added to the lipid in aliquots. The homogenization is allowed to proceed until the particle size of the resulting liposomes or HDLCs is achieved; i.e., about 1 um to about 10 um, preferably 4 um to about 6 um.

Another method is a modified MLV procedure whereby the above-produced drug-lipid film is dried in a bell Jar under reduced pressure to produce a drug-lipid flake. This flake is pulverized to a powder which is homogeneously hydrated when aqueous solution is added. This procedure involves solution of the drug in an organic solvent such as DMSO or methanol followed by mixing with a lipid (most preferably a 7:3 mole ratio of DMPC:DMPG) in methylene chloride. The mixture is then dried under reduced pressure to a film, which is then dried, for example, in a bell Jar under reduced pressure. The resulting dried powder is hydrated with an aqueous saline solution and heated to produce a drug-lipid suspension. As discussed hereinabove, the formation of HDLCs, liposomes, and mixtures thereof, and concomitant degree of toxicity, depends on the drug:lipid ratio.

Other methods may be used in the formation of HDLCs. One such method is an SPLV procedure wherein the drug is dissolved in a solvent such as DMSO. A lipid (such as a 7:3 mole ratio of DMPC:DMPG) in a solvent (e.g., chloroform or methylene chloride) is dried to a thin film under reduced pressure, and an organic solvent such as methylene chloride is added to the lipid. An aliquot of the drug (e.g., amphotericin B) in solution is added to the lipid suspension and the resulting mixture is sonicated to clarity. A buffered aqueous solution (e.g., buffered saline) is added and the mixture is again placed under reduced pressure to remove the methylene chloride. The resulting paste is hydrated ratio of drug:lipid employed. $LD_{50s}$ in mice using this preparation further with PBS and sonicated to clarity. As with the above procedure, the resulting preparation will be HDLC or liposomal depending on the mole showed lower toxicities with higher drug:lipid ratios.

Yet another method is a modified SPLV procedure wherein the drug in organic solvent (e.g., DMSO) is mixed with lipid (e.g., DMPC:DMPG) in solution, and a buffered aqueous solution (e.g., PBS) was added, followed by evaporation of the solvent under nitrogen while sonicating. Additional PBS is added and the resulting solution filtered, preferably through a 5 micron filter, then centrifuged at about 10,000×g for about 10 minutes. The supernatant solution was removed, discarded, and the pellet resuspended in aqueous solvent (PBS). Following a second "wash" by centrifugation, the resulting pellet is resuspended in PBS. As with the above-disclosed preparations, the acute toxicity of the preparations are directly related to the drug:lipid ratio; that is, the higher the ratio (to about 60 mole percent drug), the less toxic the preparation.

Yet another SPLV method is a preparation wherein the drug-solvent and lipid solutions are mixed as before, but water for injection, USP, rather than saline is added and the suspension warmed to 37° C. The solvent is again evaporated under nitrogen while sonicating, more water for injection was added, and the suspension held for about 10 minutes at 37° C. The preparations are sterile filtered through a 0.1 or 0.15 micron filter using the LUVET method. Such method is an extrusion procedure whereby liposomes are produced by filtration at pressures of about 700 psi, and is the subject of Cullis et al., PCT Publication No. 86/99238, published Jan. 16, 1986, relevant portions of which are incorporated herein by reference. Such preparations may also be dehydrated according to the methods of Bally et al., as described hereinabove. Acute toxicity tests again demonstrate the ameliorative effects of a high drug:lipid ratio on the drug toxicity.

A further method involves the dissolution of drug in acidified anhydrous ethanol by sonication. A lipid (e.g., a 7:3 mole ratio of DMPC:DMPG) dissolved in a solvent (e.g., benzene:methanol) is lyophilized, then vortically mixed with an aqueous solvent (e.g., PBS), and the acidified alcohol-drug solution added and stirred at room temperature. The preparation is then lyophilized and rehydrated with aqueous buffer. Alternatively, the solvent can be evaporated leaving a lipid-drug film, which can be hydrated with an aqueous solution. Again, lower acute toxicities are associated with preparations of higher drug:lipid ratios. When a drug concentration of about 5 mole percent and below is used, the process produces mostly liposomes, compared to the use of about 6 mole percent and above, which forms mainly HDLCs. Centrifugation of the preparation on a density gradient confirms that all the lipid is associated with the drug. The preparation may then be lyophilized, which removes the ethanol, and rehydrated in aqueous solution such as distilled water.

In another liposome forming embodiment of the present invention, amphotericin B is incorporated into liposomes via an aqueous intermediate. In this technique, amphotericin B is suspended in an aqueous solution, for example distilled water, by sonication. The suspended drug is then admixed with a suspension of lipid in aqueous solution, such as distilled water or sodium chloride solution. The mixture is incubated at or above the transition temperature of the lipid employed, with the resultant formation of vesicles.

Where dimyristoylphosphatidylglycerol (DMPG) is used alone or in combination to form the liposomes, and when the lipid has been admixed with an aqueous solution having an ionic strength of about 0 mM to about 25 mM salt, and incubated at about the transition temperature ($T_c$) of the lipid (i.e., at about 22°–24° C.), the liposomes spontaneously vesiculate, forming large unilamellar vesicles (LUVs). This method for formation of LUVs, which employs no harsh treatment of the vesicles such as exposure to chemicals, detergents, or extreme pH, is disclosed in U.S. patent application Ser. No. 136,267, filed Dec. 22, 1987 now U.S. Pat. No. 4,963,297, relevant portions of which are incorporated herein by reference.

For example, DMPG can be used alone or, for example, with other lipids such as with DMPC, e.g., in a 3:7 mole ratio of DMPC:DMPG. These lipids can be co-lyophilized from a 70:30 v/v solution of benzene:methanol, and stored at −20° C. until use. MLVs are prepared by hydrating the lipid (for example, a total of lipid of 13.5 umoles/ml) in aqueous solution such as distilled water or buffer at 4° C. When formation of amphotericin B-containing LUVs is desired, the lipid is hydrated in an aqueous solution of ionic strength of about 0 mM to about 25 mM salt, and incubated at about 23° C. Amphotericin B, dispersed in distilled water by bath sonication, at a concentration of about 0.98 umoles/ml is then added to the hydrated lipid and incubated at about 23° C. for about one hour, resulting in LUVs containing amphotericin B. These proportions of lipid and amphotericin B result in about a 7 mole % ratio of amphotericin B.

Figure 10:
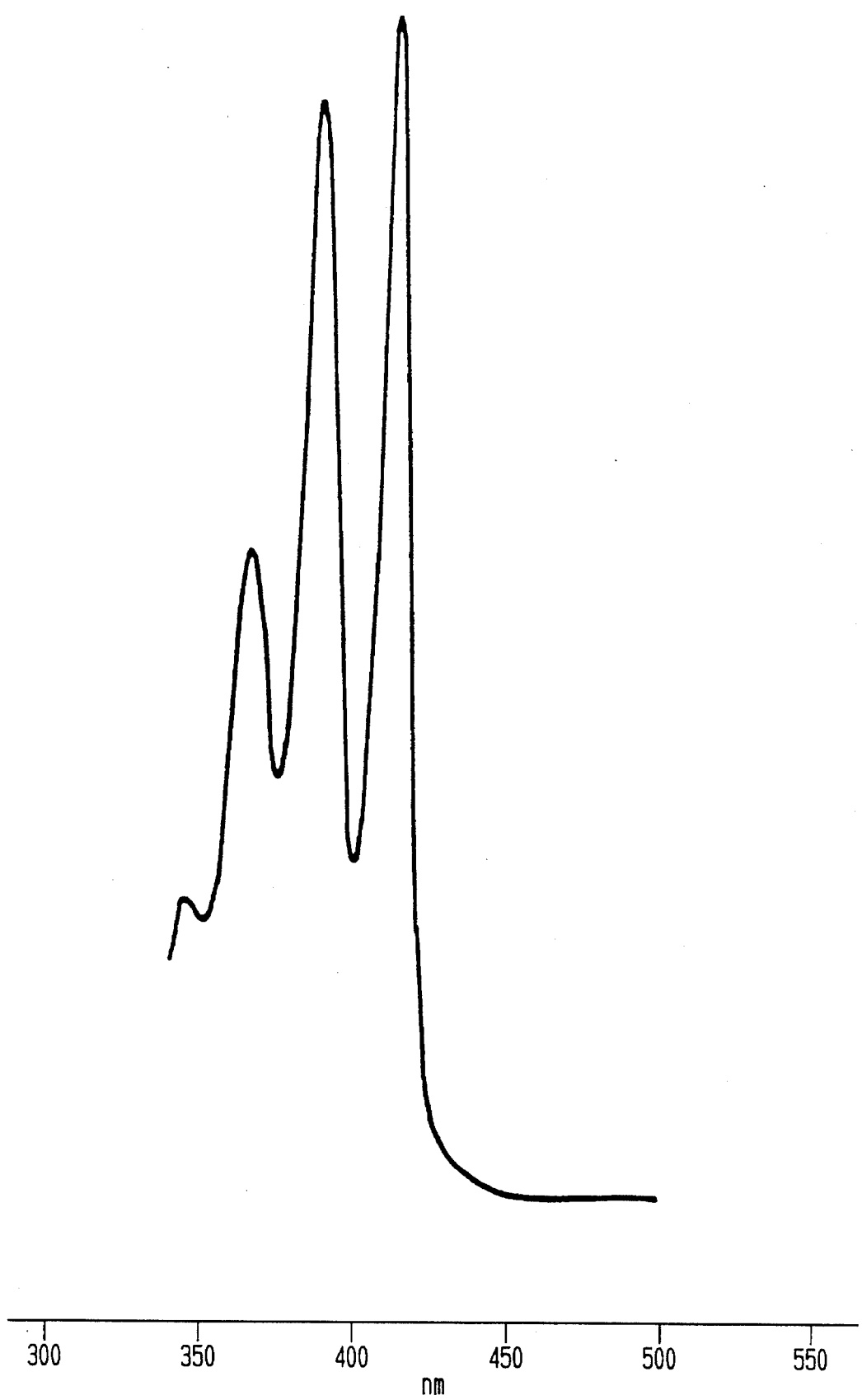
FIG. 10 is an absorbance spectrum of free amphotericin B dissolved in deoxycholate.

The high mole ratio amphotericin B-lipid preparations (HDLCs) discussed above are believed to exhibit low toxicity because of enhanced amphotericin B-amphotericin B interactions in the lipid matrix. This can be demonstrated by absorbance spectroscopy. The absorbance at 413 nm, for instance, arising from free amphotericin B in deoxycholate is greater than that for unheated 5 mole % amphotericin B in lipid. Further, the absorbance of 25 mole % amphotericin B is greater than that exhibited by 50 mole % amphotericin B in lipid (see FIG. 10).

Figure 12:
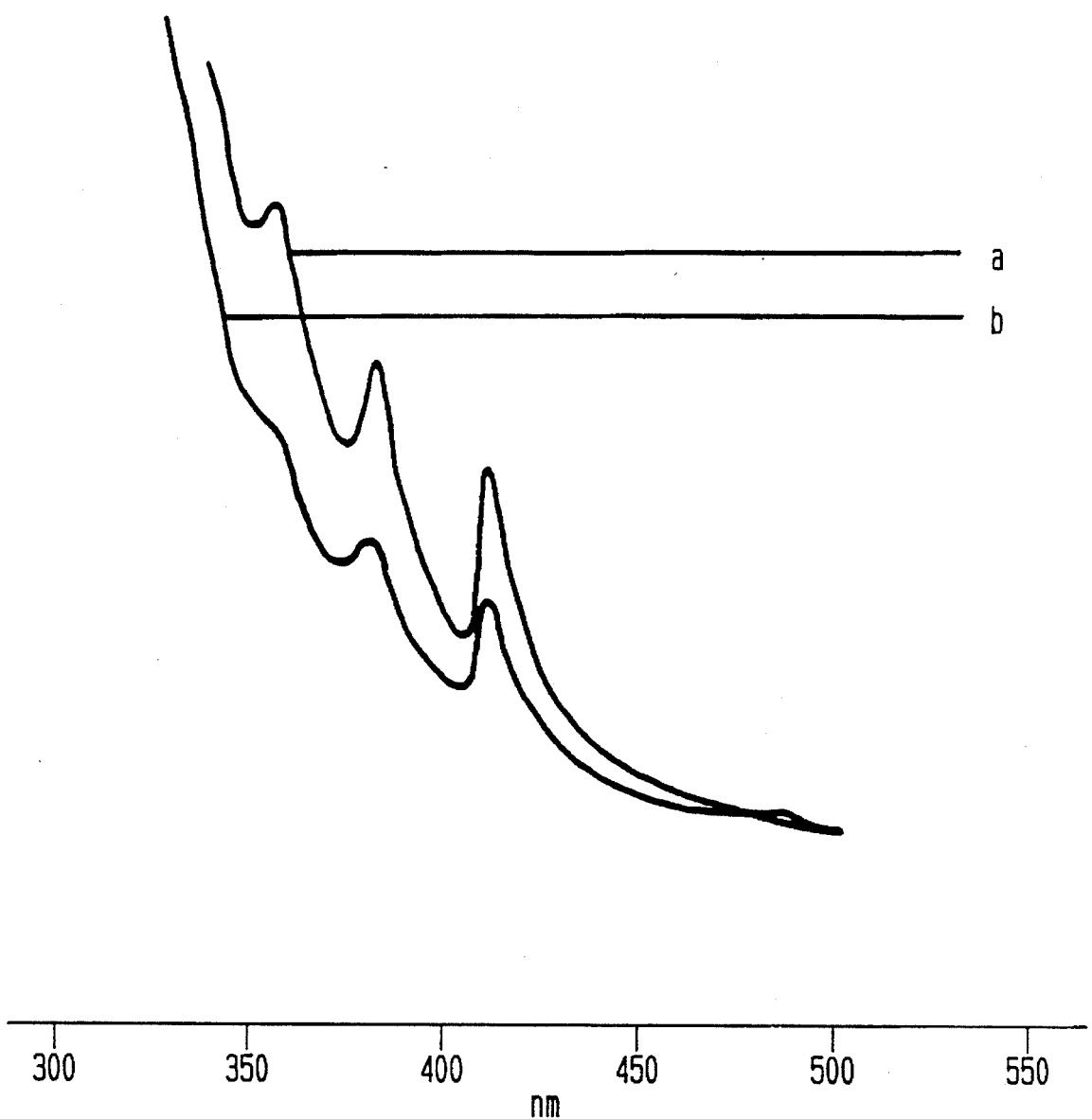
FIG. 12 is an absorbance spectrum of 25 mole % amphotericin B in 7:3 DMPC:DMPG both before (a) and after (b) heating for 10 minutes at 60° C.

The absorbance spectrum technique is used to determine the toxicity of a drug (e.g. amphotericin B)-lipid complex. The absorbance spectrum of a drug is specific for that drug; the signature of amphotericin B, (appearing in FIG. 12, dissolved in deoxycholate), is between 300 and 500 nm, and has characteristic peaks, the most representative of these peaks the one arising at 413 nm. The attenuation of this peak by complexing the drug with a lipid can be used quantitatively as a measure of toxicity of the HDLC. Any of the above-named lipids, when complexed in this way, would be expected to result in the characteristic, albeit attenuated, absorbance discussed here, since the spectra are specific to the drug.

Figure 11:
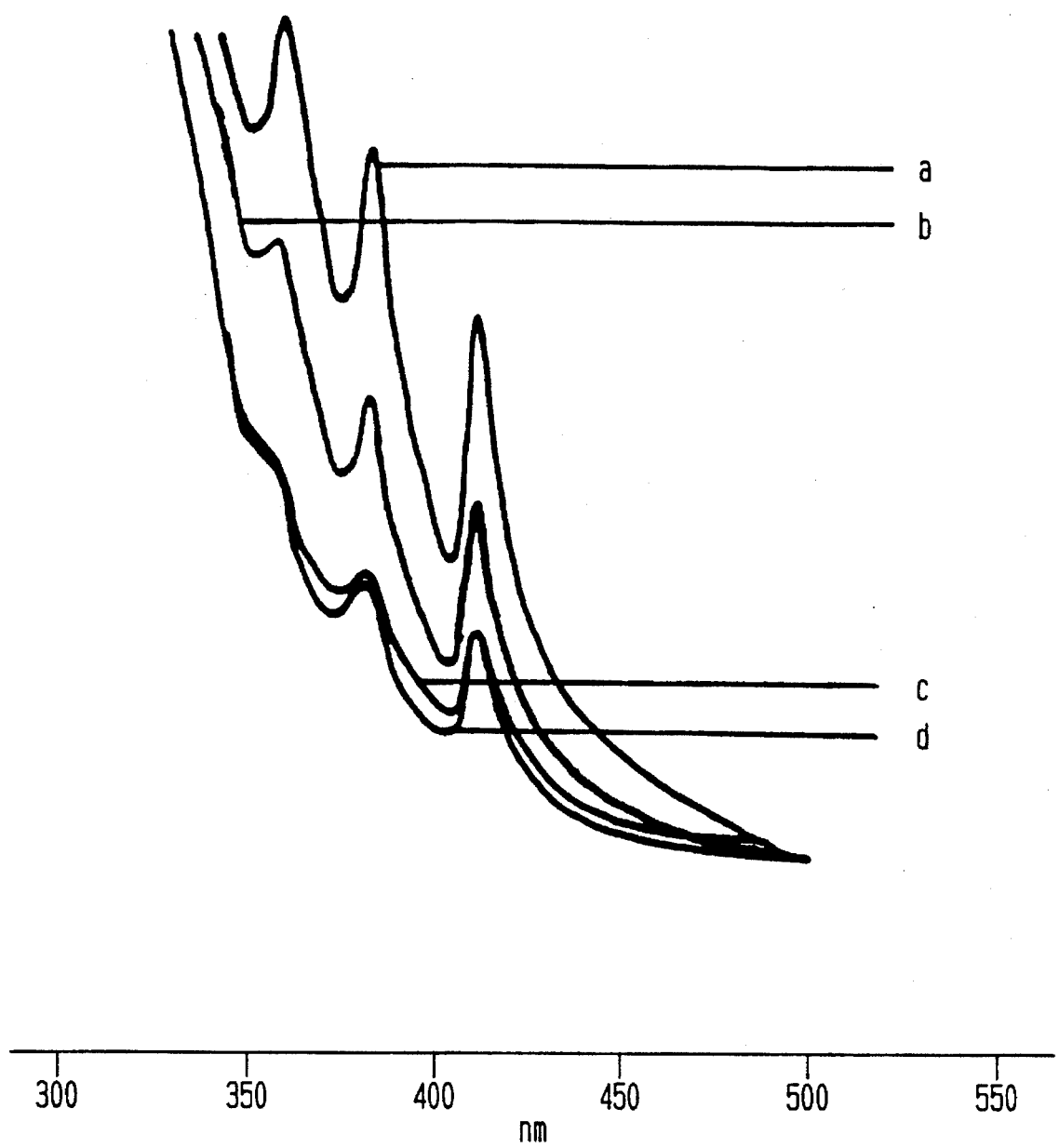
FIG. 11 are absorbance spectra of 5 mole % amphotericin B (a), 25 mole % amphotericin B (b), 25 mole % amphotericin B after heating (c), and 50 mole % amphotericin B (d), in 7:3 DMPC:DMPG.
Figure 13:
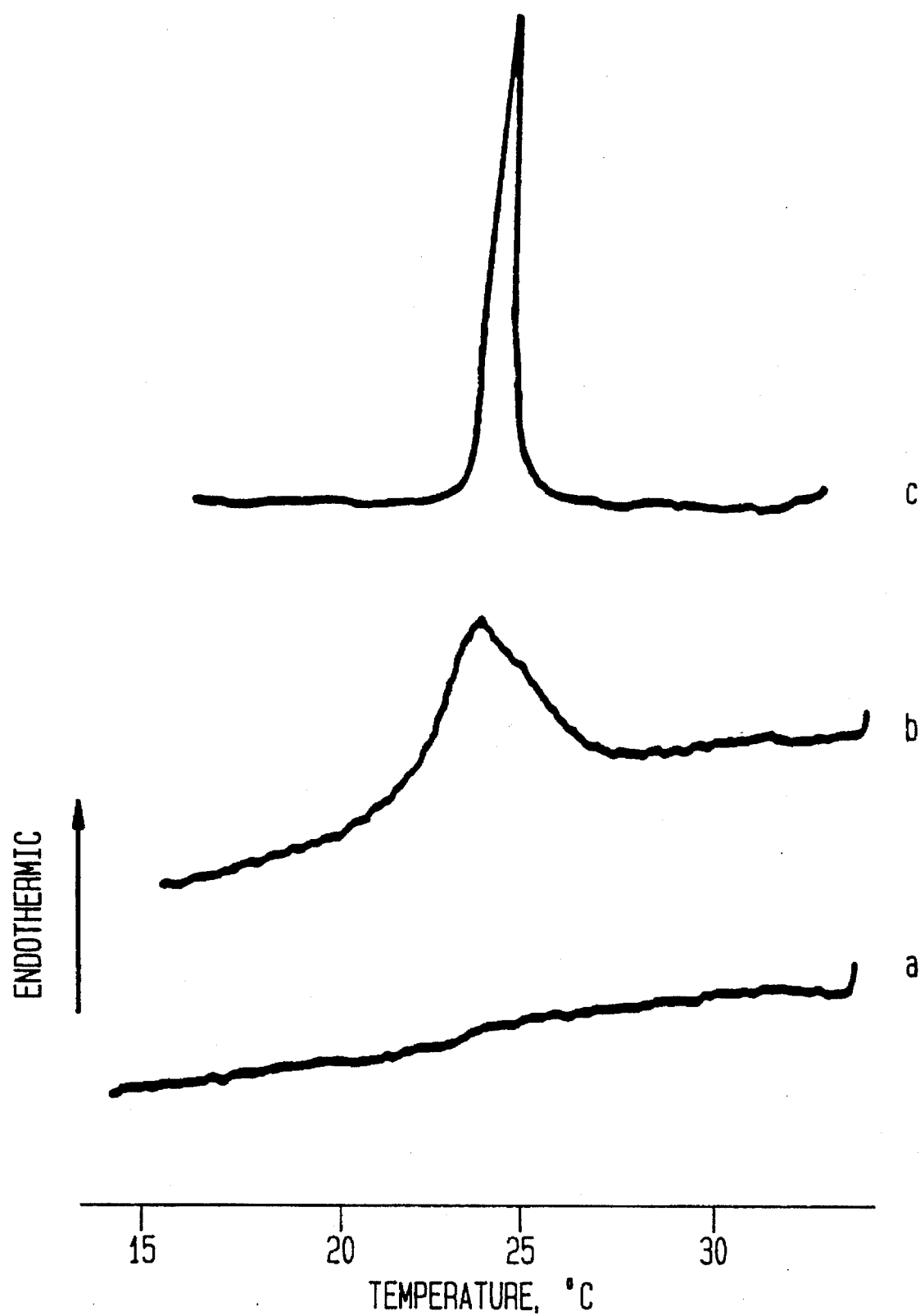
FIG. 13 is a DSC spectrum of 7:3 DMPC/DMPG containing 25 mole % amphotericin B both before (a), and after (b) heat cycling, as compared to the spectrum of pure DMPC/DMPG (c).
Figure 14:
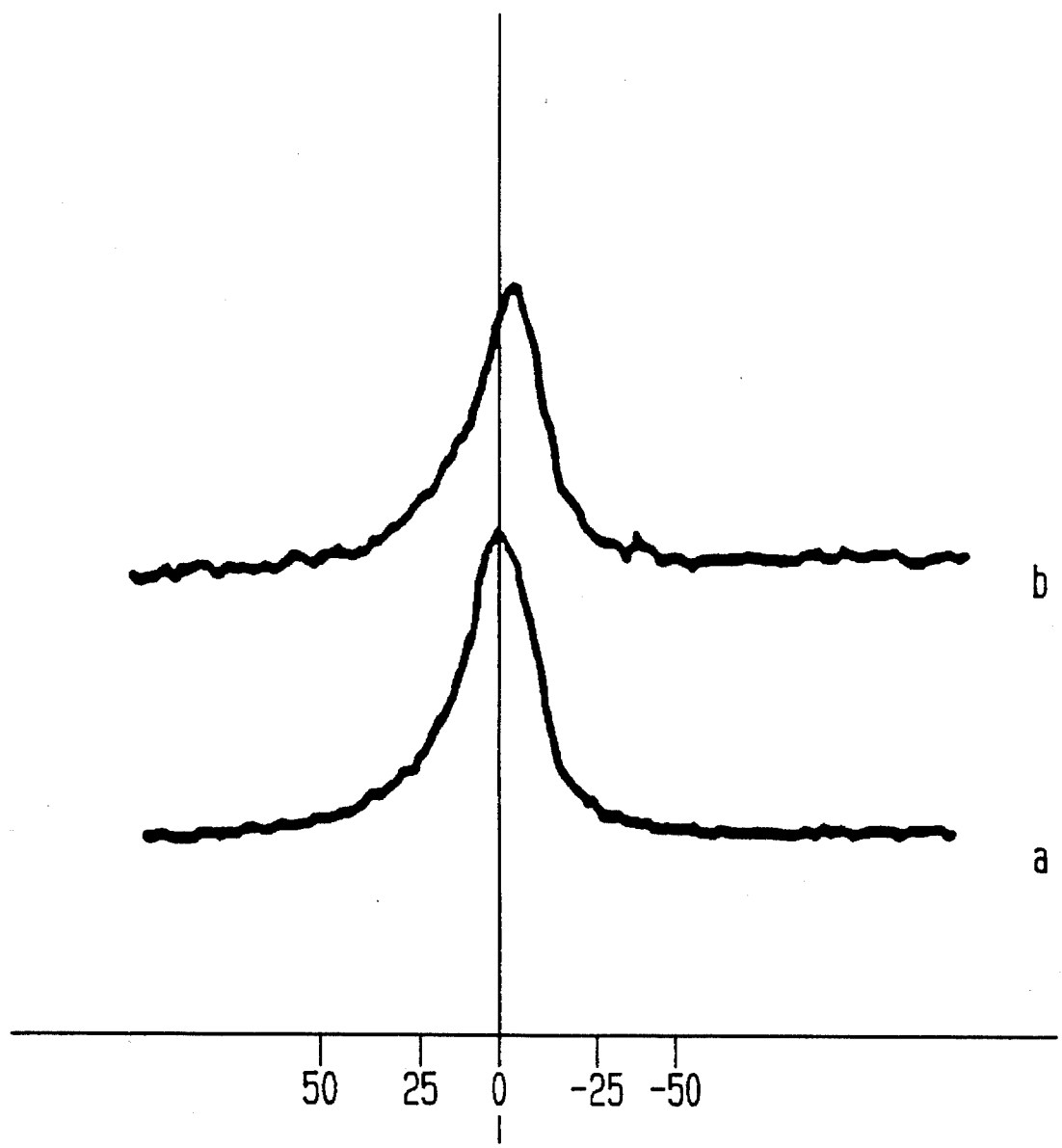
FIG. 14 is a $^{31}$P-NMR spectrum of complexes of 7:3 mole ratio DMPC/DMPG containing 25 mole % amphotericin B before (a) and after (b) heat cycling at 60° C.
Figure 15:
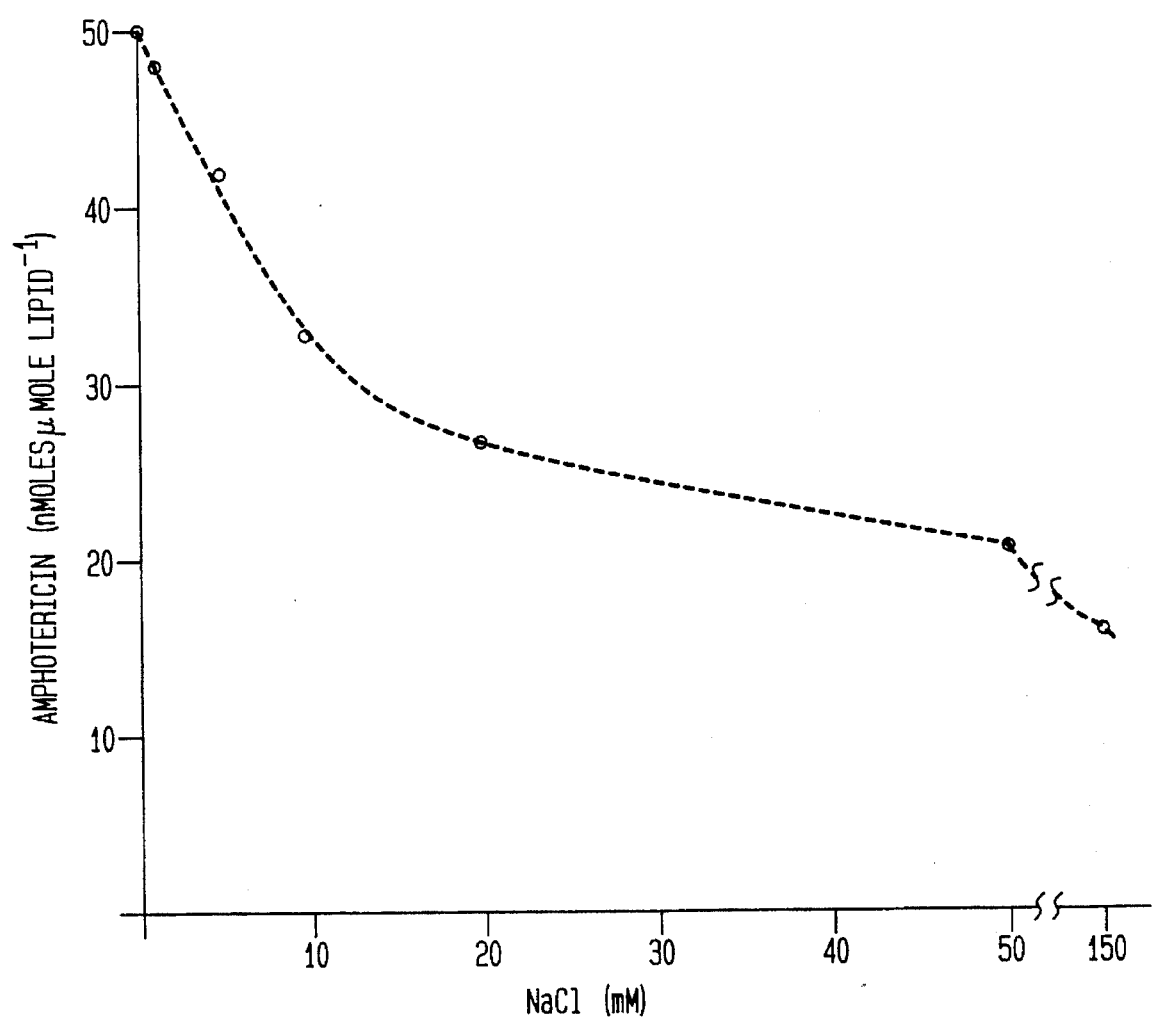
FIG. 15 is a graph demonstrating the influence of ionic strength on the uptake of amphotericin B into DMPC:DMPG liposomes.

If amphotericin B-lipid systems exhibiting less than maximal toxicity buffering (for example, 25 mole % samples), are heated to 25°–60° C., the toxicity of the resulting system is attenuated (see FIG. 11). This attenuation proceeds to a maximum of the toxicity observed when amphotericin B is complexed with 50 mole % lipid (see FIG. 11). One possible explanation is that this attenuation occurs because lipid is phase separated and thereby expelled from the amphotericin B in the heating step, allowing closer association of the amphotericin B with itself and thus a less toxic system. The expelled lipid is demonstrated by the reappearance (after heating) of an endotherm viewed in differential scanning calorimetry spectra (see FIG. 12), consistent with lipid substantially free of amphotericin B. Further, the expelled lipid can be demonstrated by the narrowing of the $^{31}$P-NMR signal arising from the heated systems (see FIG. 13). Again, this narrowing is consistent with lipid substantially reduced in amphotericin B concentration.

Finally, freeze fracture electron microscopy of heated systems reveals the existence of lipid (and liposomes) after heating, not previously observed. The unheated sample demonstrates complexes with no free lipid, characteristic of systems exhibiting intramolecular interaction between the lipid and the amphotericin B.

When the above studies were performed on samples containing 50 mole % amphotericin B, small differences were observed between samples studied before and after heating. Presumably, at the 50 mole % level, the interaction of the drug with the lipid is so great that there is no further lipid available to be expelled from the structure. These samples, then, demonstrate substantially unchanged signals both before and after heating when studied by DSC and NMR.

The theory that the phase separated lipid leaves the amphotericin B in an environment more conducive to amphotericin B-amphotericin B interaction (and thus less toxic) can be supported by absorbance spectroscopy. The spectra arising from heated systems are much less intense (signifying lowered toxicity) compared to untreated systems. In one case such heating resulted in an $LD_{50}$ of greater than 30 mg/kg as compared to an unheated preparation with an $LD_{50}$ of 15 mg/kg. In this case attenuation of absorbance at 413 nm was noted after heating.

The above heating process may be demonstrated with any type liposome or lipid particle or liposome or lipid particle formation process such as any of those previously enumerated, but in this example the MLV process was used. Similarly, any of the previously named lipids or phospholipids may be used, as may any solvents or aqueous buffers as named hereinabove. For example, lipid (in any amount known to form liposomes, such as DMPC:DMPG in a 7:3 mole ratio), suspended in an organic solvent such as chloroform, is dried to a thin film on the sides of a round bottom flask. Amphotericin B (or any other drug as previously described) is dissolved in any appropriate organic solvent (an appropriate solvent being one that dissolves the drug, specifically, for example, the amphotericin B). In the present invention, any mole % of drug (amphotericin B) that forms liposomes or lipid particles may be used. Specifically, in the present invention, from about 5 to about 50 mole % amphotericin B is used. Where liposomes are to be formed, a drug to lipid mole ratio of 5 mole % drug and less is employed. For the formation of HDLCs, about 6 to about 50 mole percent drug is employed. At 25 mole % drug and above, the population is substantially HDLC in nature.

In the present heating aspect of the invention, amphotericin B was dissolved in methanol at 10 mg amphotericin B per 100 ml methanol, or 0.1 mg/ml of amphotericin B. The methanol containing dissolved amphotericin B (100.0 ml) was added to the lipid film, and the film resuspended. The resulting suspension is then rotoevaporated under reduced pressure, to a thin film. The lipid-amphotericin B film is then resuspended in an aliquot of aqueous solution the volume of which is sufficient to form liposomes or lipid particles, such as for example about 4.0 ml. The suspension may then be agitated and sonicated for several minutes to about one hour, and heated in a water bath at from about 25° C. to about 60° C., for about 10 to about 400 minutes.

Another method for forming the HDLCs of the invention include those employing a homogenization step rather than sonication. For example, the HDLCs may be made according to the SPLV process, wherein a drug (e.g., amphotericin B) may be added to an appropriate solvent (such as DMSO) and mixed with a mechanical mixer to dissolve all the drug. If necessary, the solution can then be filtered, removing any undissolved particles of the drug. A 7:S mole ratio of DMPC:DMPG may then be dissolved in an appropriate solvent (such as methylene chloride), and the lipid then admixed with the drug-DMSO solution. An aqueous solution such as saline is then added to the mixture, and the organic solvents removed by rotary evaporation at about 35°–45° C. Following solvent removal, the resulting drug-lipid mixture is diluted with aqueous solution, such as saline, and the suspension of HDLCs milled using a homogenizer. Any homogenization device or colloid mill that will mill particles is acceptable for this procedure, but preferably a Gifford Wood colloid mill is used. The particles are milled until an acceptable particle size has been achieved, for example, wherein 90% of the particles are below 10 um in diameter, preferably within a size range of about 4 to about 10 microns, or about 15–30 minutes. The particles may passed one or a multiple number of times through the mill, depending on the size and homogeneity desired. The HDLC particles may be analyzed for size distribution using the Malvern particle sizer. If necessary, larger and smaller particles may be removed by any methods known in the art for separating particles, such as by filtration. Such a process preferably results in particles between about 0.2 um and 10.0 um in diameter.

Such a filtration method may be, for example, tangential flow filtration, such as described in U.S. patent application Ser. No. 225,327, filed Jul. 28, 1988, now abandoned Docket No. TLC-139A, entitled "Method for Size Separation of Particles". In this procedure, incorporated herein by reference, a heterogeneously sized population of liposomes or particles is passed through the tangential flow device having a filter pore size of about, for example, 5.0 um. Liposomes less than 5.0 um in size pass through the filter into the filtrate, and those greater than 5.0 um are retained in the retentate. The filtrate may then be passed through the device through a filter size of about for example, 2.0 um. In this case, the filtrate contains liposomes or particles of 2.0 um or less, while the retentate contains liposomes or particles of a homogeneous population between the sizes of 2.0 and 5.0 um. As defined in the present application, a homogeneous population of vesicles is one composed of substantially the same size vesicles, and may have a Gaussian distribution. In some cases, the size distribution of the vesicles may be unimodal. Such a population is also said to be of a uniform size distribution, and may be unimodal with respect to size. The term "unimodal" refers to a population having a narrow polydispersity of particle sizes, and the particles are of a single "mode".

A liposomal population is unimodal if, when measured by quasi elastic light scattering methods, the population has a Gaussian distribution, and if a second order polynomial will fit the natural logrithm of the autocorrelation function of a sample (Koppel, 1972, J. Chem. Phys., 57:4814). The closer this fit, the better the measure of unimodality. The closeness of this fit may be determined by how close the chi square (chi$^2$) value of the sample is to unity (1.0). A chi$^2$ value of 2.0 and less is indicative of a unimodal population.

Other methods known to those skilled in the art for forming liposomes may be used in the practice of the present invention; the invention of HDLCs is not limited solely to the above-mentioned processes for their formation.

The HDLC preparations and liposomes resulting from the novel processes of the present invention, can be used therapeutically in animals (including man) in the treatment of a number of infections or conditions which require: (1) repeated administrations; (2) the sustained delivery of a drug in its bioactive form; or (3) the decreased toxicity with substantially equivalent or greater efficacy of the free drug in question. Such conditions include but are not limited to fungal infections, both topical and systemic such as those that can be treated with antifungal agents such as nystatin and amphotericin B and the viral diseases acquired immunodeficiency syndrome (AIDS) and herpes. Additionally, the preparations of the invention are stable in aqueous solution.

The mode of administration of the preparation may determine the sites and cells in the organism to which the compound will be delivered. The HDLCs and liposomes of the present invention can be administered alone but will generally be administered in admixture with a pharmaceutical carrier selected with regard to the intended route of administration and standard pharmaceutical practice. For instance, delivery to a specific site may be most easily accomplished by topical application (if the infection is external, e.g., on areas such as eyes, skin, in ears, or on afflictions such as wounds or burns). Such topical applications may be in the form of creams, ointments, gels, emulsions, or pastes, for direct application to the afflicted area. Alternatively, the preparations may be injected parenterally, for example, intravenously, intramuscularly, or subcutaneously. For parenteral administration, they can be used, for example, in the form of a sterile aqueous solution which may contain other solutes, for example, enough salts or glucose to make the solution isotonic. Other uses, depending on the particular properties of the preparation, may be envisioned by those skilled in the art.

The compositions of the invention can be used for the treatment of asthma, by instilling a nebulised aqueous suspension of the liposomes or HDLCs into the lungs. For example, the liposomes or HDLCs can be suspended in a suitable solvent which can be aerosolized by a pneumatic or ultrasonic nebulizer, or, more conveniently, by a self-contained nebulizer that is driven by gas pressure from a fluorocarbon pellet. Other inhalation systems, such as those in which the liposomes or HDLCs are delivered in particle form, either as a dry powder or as a suspension in a suitable carrier system are acceptable. Following aerosolization, most of the propellant solvent is lost through flash evaporation and replaced by moisture in the respiratory tract, leading to the deposition of the particles.

For administration to humans in the curative or prophylactic treatment of fungal or viral diseases, the prescribing physician will ultimately determine the appropriate dosage for a given human subject, and this can be expected to vary according to the age, weight, and response of the individual as well as the nature and severity of the patient's symptoms. The dosage of the drug in the HDLC or liposomal form will generally be about that employed for the free drug. In some cases, however, it may be necessary to administer dosages outside these limits.

The following examples are given for purposes of illustration only and not by way of limitation on the scope of the invention.

EXAMPLE 1

Amphotericin B (10 mg; total drug 5 mole percent) was added to 100 ml of methanol in a 500 ml round bottom flask and the mixture sonicated until clear. This sonicating step was performed in a bath sonicator for about 15 minutes at 25° C., at about 50–60 Hz. Dimyristoylphosphatidylcholine (DMPG) was added (100 mg in 1.0 ml of chloroform) as well as 42 mg of dimyristoylphosphatidylglycerol (DMPG) (in 0.42 ml chloroform). The resulting dispersion was dried by rotary evaporation at 60° C. under reduced pressure, to produce a thin film in the flask. The film was resuspended in 4.0 ml of PBS, the solution transferred to a glass tube and sonicated to clarity.

The above example was repeated with 16.7, 20, 25, 33, 50 and 60 mole percent amphotericin B. Acute toxicity studies ($LD_{50s}$), which measure the dosage of drug producing a 50% death rate in mice, were higher as the mole percent of drug was increased, up to 50 mole percent amphotericin B.

EXAMPLE 2

Amphotericin B (140 mg; total drug 5 mole percent) was added to 1.5 ml dimethyl sulfoxide (DMSO). DMPC (1400 mg) and 600 mg DMPG were dissolved in 50 ml methylene chloride, and the two solutions were transferred to a flask. The solution was mixed until clear and then dried by rotoevaporation under reduced pressure to produce a film on the flask, then dried 1–4 days in a bell Jar. After such drying, the film, which had formed dried flakes, was pulverized to a powder and mixed with 100 ml or 50 ml of 0.9% saline, or 50 ml of USP water for injection. The resulting suspension was heated at 37° C. for one hour.

The above example was repeated using methanol rather than DMSO as the suspending solvent for amphotericin B, and at mole percents of amphotericin B of 10, 16.7, and 33. One gm and 2 gm of egg phosphatidylcholine was used in place of the 7:3 mole ratio of DMPC:DMPG.

EXAMPLE 3

Amphotericin B (100 mg; total drug 5 mole percent) was dissolved in 2.0 ml of DMSO. DMPC (100 mg in 1.0 ml) and DMPG (42 mg in 0.42 ml) were codissolved in chloroform in a flask and the chloroform removed by rotoevaporation under reduced pressure. Methylene chloride (20 ml) was added to the flask followed by the addition of 0.2 ml of the stock amphotericin B solution. This suspension was sonicated to clarity (about 1 minute) under the conditions as stated in Example 1. PBS (0.3 ml), pH 7.2, was added and the methylene chloride was then removed under a stream of nitrogen while sonicating. The resulting paste was resuspended in 10.0 ml PBS and centrifuged at 10,000×g for 10 minutes, followed by bath sonication for about 20 minutes.

The above example was repeated using 16.7, 20, 25, 33, 50, and 60 mole percent amphotericin B.

EXAMPLE 4

Amphotericin B (140 mg, total drug 5 mole percent) was dissolved in 1.5 ml methylene chloride. The two solutions were mixed until clear, transferred to a flask, and mixed with 8.0 ml of PBS. Methylene chloride was evaporated under a nitrogen stream while in a bath sonicator. Sonication proceeded as in Example 1. PBS (32 ml) was added and the solution filtered with a 5 micron pore polytetrafluoroethylene (PTFE) TEFLON filter, washed by centrifugation twice, and finally suspended in 100 ml PBS.

The above example was repeated using 4.0 and 12.0 ml of PBS to hydrate the lipid.

EXAMPLE 5

Amphotericin B (140 mg; total drug 5 mole percent) was dissolved in 1.5 ml DMSO. DMPC (1400 mg) and 600 mg of DMPG were dissolved in 50 ml methylene chloride. The two solutions were mixed until clear, transferred to a flask, and dried to a thin film by rotoevaporation under reduced pressure. The film was then resuspended in 50 ml methylene chloride, and 8.0 ml PBS was added to this solution. Methylene chloride was removed by evaporation under nitrogen while sonicating, according to the procedure of Example 1. The resulting paste was further hydrated with 32 ml PBS, and the suspension washed by centrifugation twice, finally resuspended in 100 ml PBS, and passed through a 5 micron pore size TEFLON (PTFE) filter.

The above example was repeated using glycine buffer at pH 3, 6, and 9 in place of the PBS.

The above example was also repeated using 5.0, 10.0, 15.0, 20.0 ml of PBS as the volume of hydrating buffer.

EXAMPLE 6

Amphotericin B (140 mg; total drug 5 mole percent) was dissolved in 1.5 ml DMSO. Egg phosphatidylcholine (EPC) (2.0 gm) was dissolved in 50 gm methylene chloride, and the two solutions mixed in a flask. PBS (8.0 ml) was added and the solvent removed under a nitrogen stream while sonicating, according to the procedure of Example 1. PBS (200 ml) was added.

The above example was repeated using 10 and 20 mole percent amphotericin B.

EXAMPLE 7

Amphotericin B (140 mg; total drug 5 mole percent) was dissolved in 1.5 ml DMSO. DMPC (1400 mg) and 600 mg DMPG were dissolved in a 500 ml round bottom flask with 50 gm methylene chloride. The two solutions were mixed in a flask, and 10 ml water for injection, USP, at 37° C., was added. The solvent was evaporated using a nitrogen stream while sonicating, according to the procedure of Example 1, and 50 ml of water for injection, USP, was then added, and the solution warmed to 37° C. for 30 minutes.

The above example was repeated using 10 and 16.7 mole percent amphotericin B, followed by the passage of the solution through a 3 micron straight-through path polycarbonate filter, available from Nucleopore.

EXAMPLE 8

Amphotericin B (140 mg; total drug 16.7 mole percent) was mixed with 50 ml methanol and the mixture sonicated 15 minutes to form a solution, then passed through a 0.22 micron tortuous path filter (mixed cellulose and acetate nitrate esters) available from Millex. DMPC (350 mg) and 150 mg DMPG were codissolved in 50 gm methylene chloride, and was mixed with the filtrate solution. The solvents were evaporated under a nitrogen stream while sonicating, according to the procedure of Example 1. PBS (50 ml) was added. Half the preparation (25 ml) was lyophilized by standard lyophilization procedures.

EXAMPLE 9

To 2.0 ml of anhydrous ethanol was added 10 ul of 1N hydrochloric acid. Amphotericin B (20 mg; total drug 5 mole percent) was added to the acidified ethanol and the mixture sonicated to clarity under the conditions as in Example 1 except for the sonication time being 30 seconds to 60 seconds. DMPC (200 mg) and DMPG (42 mg) were placed in a test tube to which was added a benzene:methanol (70:30) solution, and the solution was lyophilized as in Example 8. The dried lipid was mixed with 2.0 ml of PBS and the mixture dispersed by vortical mixing. The amphotericin B solution (0.2 ml) was added to the lipid, and the mixture stirred overnight. The resulting DMPC:DMPG MLVs (200 ul) were layered onto a sucrose density gradient and centrifuged for 24 hours at 22° C. at 230,000×g. Results are shown in FIG. 11; all the amphotericin B was associated with the lipid, in a broad distribution with the top of the gradient containing most of the lipid and the major amphotericin B peak at the bottom of the gradient. Alternatively, the resulting DMPC:DMPG MLVs were lyophilized and rehydrated with distilled water (2.0 ml).

The above example was repeated using 7, 9, 16.7, 17, 20, 25, 33, 50, and 60 mole percent amphotericin B. At the mole percent of drug at and above 16.7, mostly HDLCs were formed. Density centrifugation gradients of such high drug:lipid ratio preparations are similar to those shown in FIG. 5, where all the drug and lipid are co-associated in a single peak.

EXAMPLE 10

Samples of 25 mole percent amphotericin B-DMPC:D-MPG were prepared for x-ray diffraction, DSC, freeze fracture electron microscopy, and $^{31}$P-NMR studies as follows: A 7:3 mole ratio of DMPC:DMPG (44 mg total lipid) and 20 mg amphotericin B (25 mole percent amphotericin B) was suspended in chloroform:methanol (70:30 v/v), and was evaporated under reduced pressure at 55° C. to a thin film on the sides of a flask. The film was hydrated with 8.0 ml of 20 mM Hepes, 250 mM NaCl, pH 7.2, at 22° C. by vortical mixing with glass beads. The preparation was centrifuged at 10,000×g for 10 minutes, the supernatant decanted, and the pellet resuspended in 1.0 ml of the Hepes/NaCl buffer. The preparation was then sonicated in a bath sonicator for 20 minutes, at 25° C., 50–60 Hz.

The above procedure was repeated using 0, 5, and 50 mole percent amphotericin B.

EXAMPLE 11

To determine captured volume of amphotericin B-containing liposomes and HDLCs, the following procedure was followed:

DMPC (100 mg), and 42 mg of DMPG, both in chloroform were combined with 10 mg amphotericin B (25 mol %) in methanol (0.1 mg/ml amphotericin B) in a flask. The solvent was removed under reduced pressure at 37° C. PBS (3.7 ml), to which was added 0.3 ml of a dilute $^3$H-inulin solution in distilled water was added to the dry lipid film, with agitation. An aliquot (10.2 ml) of this solution was placed in scintillation cocktail and counted for radioactivity in a beta scintillation counter. A second aliquot was assayed for phosphate according to the method of Bartlett, J. Biol. Chem., 1959, 234:466–468. The lipid-drug suspension was centrifuged at 10,000×g for 10 minutes, the supernatant discarded, and the pellet resuspended in PBS. The centrifugation and pellet resuspension steps were carried out twice more; the last resuspension was sampled (100 ul) and counted in a beta scintillation counter. A second aliquot of the final pellet resuspension was assayed for phosphate as above. Percent entrapment of inulin was calculated by dividing final radioactive counts by starting counts and multiplying by 100. Captured volume (ul inulin entrapped/ umol lipid) was also calculated.

The above procedure was repeated using 0, 5, and 50 mole % amphotericin B.

EXAMPLE 12

Amphotericin B particles were prepared by drying 15.5 mg of DMPC and 6.5 mg DMPG (7:3 mole ratio) from about 10 ml of chloroform onto the sides of a 100 ml round bottom flask. Amphotericin B (10 mg) was suspended in 100 ml of methanol, and 100.0 ml of the methanol solution was added to the flask and the lipid film suspended, giving 25 mole % of amphotericin B. The mixture was then dried under rotoevaporation at 37° C. to a thin film on the sides of the flask. The film was then hydrated with 4.0 ml of 10 mM Hepes, 150 mM NaCl (pH 7.2) using glass beads, and sonicated for 30 minutes, to produce a final suspension. A sample of this suspension was then heated to 60° C. for 10 minutes, by immersion in a water bath. The resulting suspension was characterized by DSC, NMR, and freeze fracture electron microscopy.

The above procedure was repeated, with no heating of the sample. This sample was held at 22° C., and was also characterized by the above-named techniques.

EXAMPLE 13

The materials and procedures of Example 12 were repeated using 50 mole % and 5 mole % amphotericin B. These systems were characterized by DSC, ESR, and freeze fracture electron microscopy.

EXAMPLE 14

DSC measurements were carried out on a Micro Cal MC-1 Unit from Micro Cal, Inc., Amherst, Mass. Sample volumes of 0.70 ml containing 5–9 mg of suspension were injected into the sample cell, with the same volume of buffer used in the reference cell. Samples were heated either at about 26° C./hour or about 37° C./hour. Duplicate runs of the same sample with the same history gave onset and completion temperatures reproducible to 0.2° C. In general, samples containing amphotericin B were heated to 60° C., (no higher) and then cooled to 7°–4° C. for at least 2 hours in order to insure consistent sample history.

EXAMPLE 15

NMR spectra were obtained at 145.7 MHZ on a Bruker AM360 wide bore NMR spectrometer using 8K data points for acquisition, a sweep width of 50,000 HZ and a pulse width of 20 usec corresponding to a 45° pulse. Spectra were accumulated from up to 10,000 transients.

EXAMPLE 16

A 0.1–0.3 ul aliquot of the specimen was sandwiched between a pair of Balzers (Nashua, N.H.) copper support plates and rapidly plunged from 23° C. into liquid propane. Samples were fractured and replicated on a double replicating device in a Balzers freeze-fracture unit at a vacuum of $2\times10^{-6}$ mbar or better and at −115° C. Replicas were floated off in 3N $HNO_3$, followed by washing in a graded series of sodium hypochlorite solutions. These were finally cleaned in distilled water and picked up on 300 Hex mesh copper grids (Polysciences, Pa.). Replicas were viewed on a Philips 300 electron microscope at a magnification of 3,000 to 22,000 times.

EXAMPLE 17

Absorbance spectra (as in FIGS. 12 and 13) were made by diluting amphotericin B in Hepes/NaCl buffer to 25 uM liter amphotericin B. A sample was placed in the sample cuvette of a Beckman Spectrophotometer and read at 300 to 500 nm. The sample cuvette was read against a buffer blank.

EXAMPLE 18

Samples for ESR were labeled with a series of positional isomers of doxyl steric acids where the doxyl reporter group was present at different positions along the fatty acid chain. Labelling was effected by incorporating the probe by vortexing and sonication from an ethanolic solution which was dried to a thin film on the side of a test tube. All samples were labeled to one mole percent.

ESR spectra were recorded on an IBM Instruments ER100D ESR Spectrometer with nitrogen gas flow temperature regulation. An external calibrated thermistor (Omega Engineering, Inc., Stamford, Calif.) was used to monitor the temperature of the sample. ESR spectra were recorded at a microwave power of 10 MW and a microwave frequency of 9.11 GHZ with a field sweep of 100 G and a 100 KHZ field modulation amplitude of 0.32 G. The order parameter was calculated from the maximum hyperfine splitting (A max).

EXAMPLE 19

Amphotericin B (337.5 g) was added to 3375 ml of DMSO and the amphotericin B (100 mg/ml) mixed to dissolution (about 3 hours) using a mechanical mixer. The mixture was transferred to a stainless steel pressure vessel (5 L capacity) and filtered through 0.22 um Sartofluor filter and polypropylene depth filter (Pall Profile, Pall, Inc., Glen Cove, N.Y.).

In a 40 L pressure vessel, 50.8 kg of methylene chloride was mixed with 225.0 gm of DMPC and 99.0 gm of DMPG, for 3.5 hours to completely dissolve. The resulting lipid solution was transferred through a 0.2 $M^2$ Sartofluor 0.22 micron TEFLON® (tetrafluoroethylene) filter into a stainless steel processing tank. The 40 L pressure vessel was washed with an additional 55.2 kg of methylene chloride, and similarly filtered into the processing tank. The processing tank was set to rotary mix the lipid solution at 195 rpm, and the amphotericin B DMSO solution was then transferred to the tank. Sodium chloride solution (16.2 L, 0.97% USP) was then added to the tank through a 0.22 um Millipak 100 polycarbonate filter.

Using a heat exchanger set at 35° C. in series with the processing tank, a heated liquid nitrogen stream was passed across the tank and the solvent was removed over a 12 hour period. The resulting lipid-drug complex was diluted with sodium chloride 0.97. USP (7000 ml) transferred to the tank through a Millipak 100 0.22 micron filter.

The resulting HDLCs were homogenized by using the Gifford Wood colloid mill and a rotary lobe pump. HDLCs were passed through the colloid mill head at an 0.5 mil gap setting with back pressure of 10 psi, for 3.0 hours, resulting in particles less than 20 microns. Particle size of the HDLCs was analyzed by the Malvern particle analyzer.

EXAMPLE 20

Lipid (102.6 umol total, 70:30 mole ratio of DMPC:DMPG dissolved in chloroform was pipetted into a 500 ml round bottom flask. Nystatin (500 mg) was dissolved in 1.0 L methanol (0.5 mg/ml) by sonication in a Branson bath sonicator. Dissolved nystatin (5.0 ml) was added to the round bottom flask containing lipid, and mixed; the solvent was then removed by rotary evaporation at 45° C. for 15 minutes, and the resulting preparations rehydrated in saline (5.0 ml) by vortical mixing with glass beads. Upon light microscopic examination, liposomes were visible.

The above was repeated using 25, 50, 75, and 100 mole % nystatin. Upon freeze fracture electron microscopic examination, the preparation containing 25 mole % Nystatin were non-liposomal HDLCs.

EXAMPLE 21

Lipid (14.8 umol/ml, 7:3 mol ratio of DMPC:DMPG) was hydrated in distilled water and incubated at 4° C. The resulting MLVs were extruded through two stacked polycarbonate filters ten times using the LUVET procedure.

Amphotericin B was dispersed in distilled water using a bath sonicator at a concentration of 10.8 umol/ml. The amphotericin B dispersion was added to the lipid suspension to a final lipid and amphotericin B concentration of 13.5 umol/ml and 0.98 umol/ml, respectively. To remove unincorporated amphotericin B, 20 ml of the sample were centrifuged at 15,000×g for 30 minutes in a Ti60 or SW 27 rotor (Beckman) at 22° C. in a Beckman L8–60 ultracentrifuge. The supernatant free amphotericin B was removed without disturbing the liposome pellet. The resulting liposomes were measured by quasi-elastic light scattering to be larger than 1.0 um in diameter.

Figure 17:
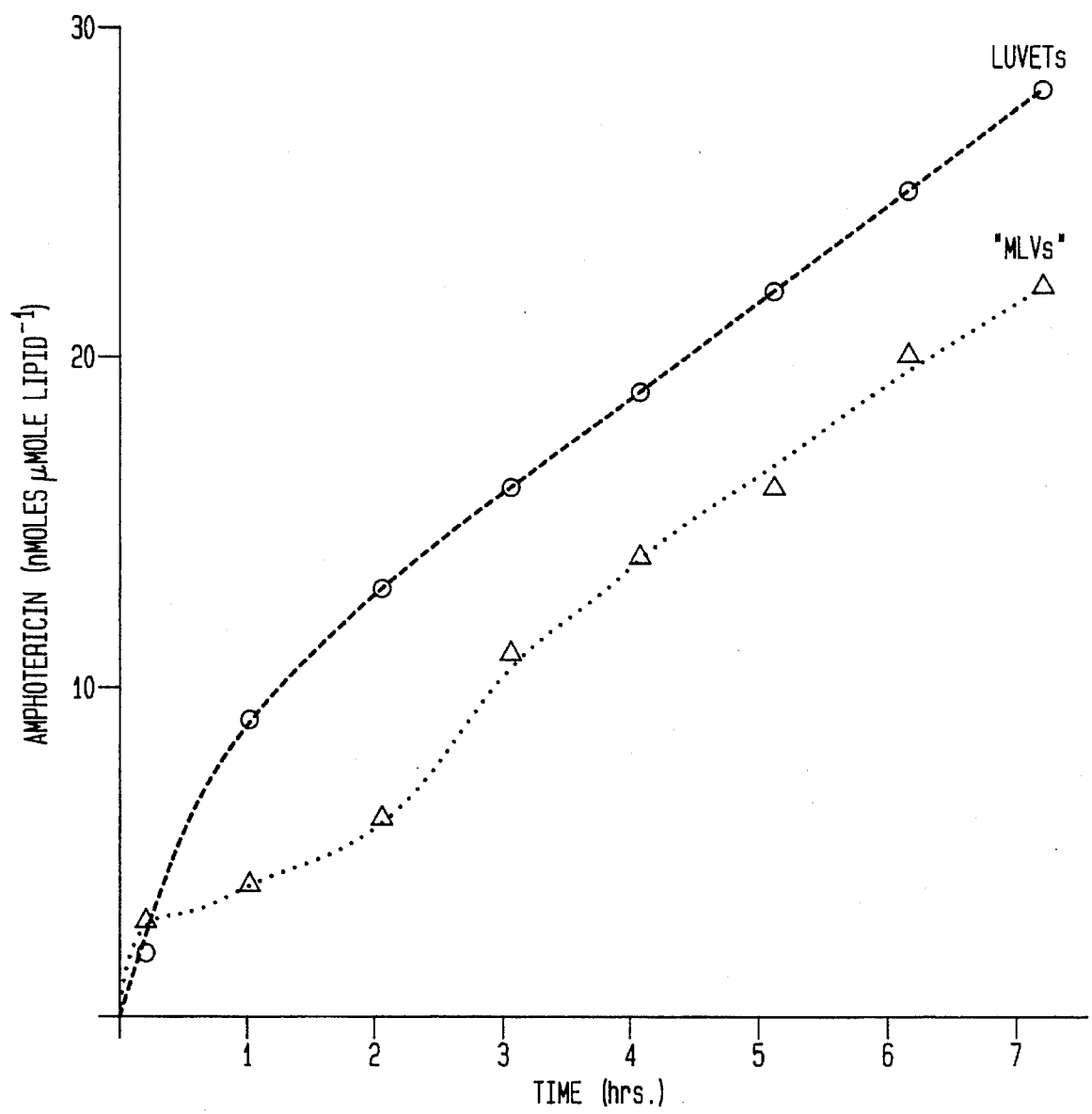
FIG. 17 shows the influence of liposome structure on uptake of amphotericin B into DMPC:DMPG MLVs or LUVs.

The above procedure employing incubation conditions of 23° C. were repeated employing 150 mM NaCl, 10 mM $Na_2PO_4$, pH 7.4 to hydrate the lipids. The resulting liposomes were measured by quasielastic light scattering to be larger than 1.0 um in diameter. Rate of amphotericin B uptake by liposomes was highest when the ionic strength of the medium was low (distilled water vs. 150 mM NaCl) (FIG. 17).

Figure 16:
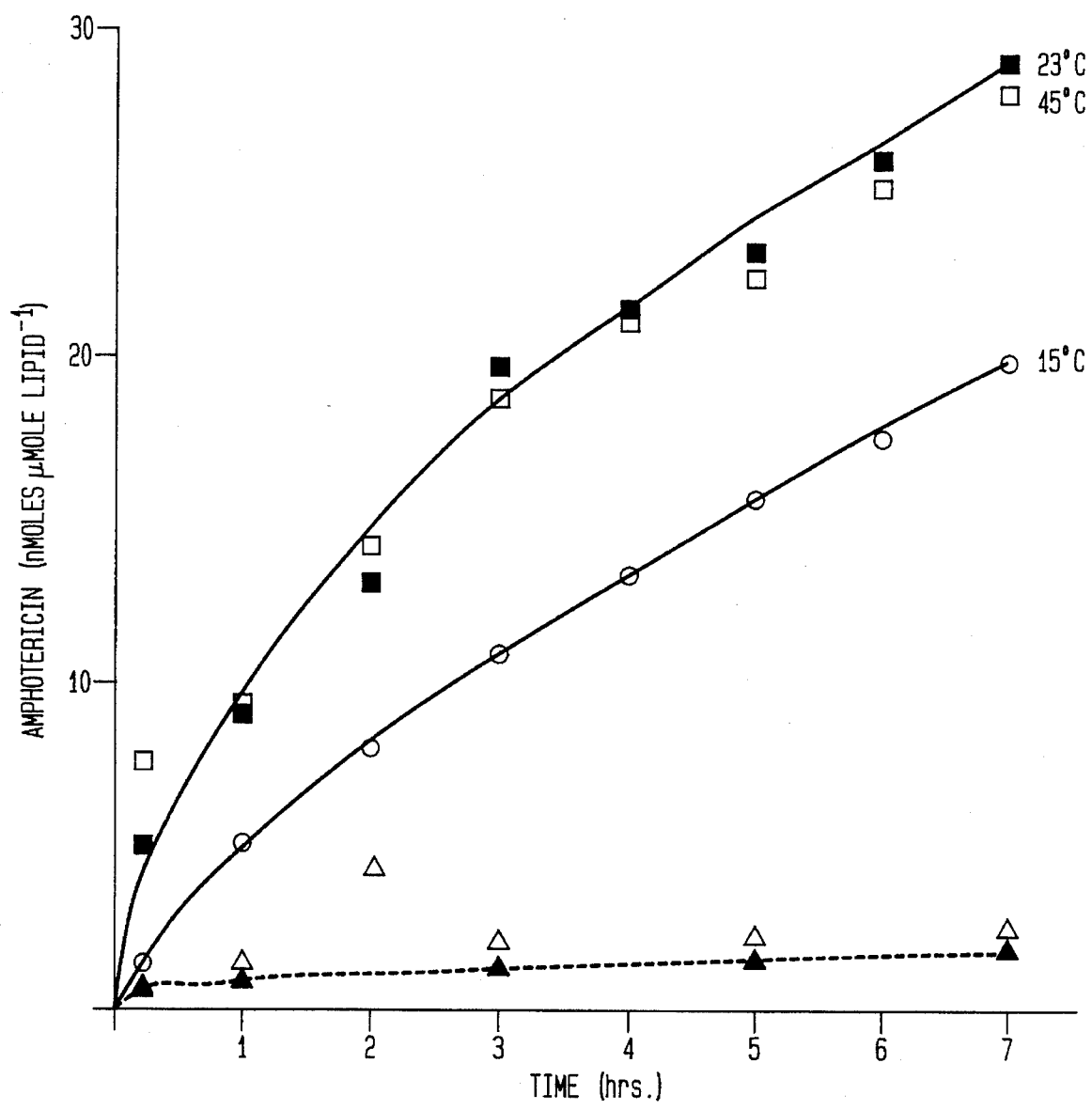
FIG. 16 shows the effect of incubation temperature on the rate of amphotericin B uptake into DMPC:DMPG liposomes.

FIG. 16 shows the uptake of amphotericin B into DMPC:DMPG liposomes under various incubation temperature conditions. Rate of uptake is similar at 23° C. and 45° C. The drug also accumulates when the lipid is in the gel phase i.e., at 15° C.

EXAMPLE 22

The materials and procedures of Example 21 were employed, but wherein the lipid suspended in distilled water was incubated with the amphotericin B at 22° C. The resulting liposomes were unilamellar and measured at about 0.1–0.2 um in mean diameter by quasi elastic light scattering. FIG. 19 shows that the rate of amphotericin B uptake is faster in the first two hours with these LUVs than with MLVs.

EXAMPLE 23

Amphotericin B particles (HDLCs) were formed according to the following procedure: Amphotericin B (337.5 g) was added to 3375.0 ml of DMSO, and stirred to dissolve for 5.5 hours at 25° C. This solution was sterile filtered into a 5 L pressure can at 25° C.

Dimyristoylphosphatidylcholine (DMPC) (264.3 g) and 109.9 g of dimyristoylphosphatidylglycerol (DMPG) (a 7:3 mole ratio) were combined with 35.2 L of methylene chloride in a 40 L pressure vessel, and mixed to dissolve completely. This solution was sterile filtered through a 0.22 um poly(perfluoroethylene) (TEFLON) filter into a 140 L processing tank. Methylene chloride (39.1 L) was sterile filtered through a 0.22 um Teflon filter and added to the 140 L tank. The amphotericin B/DMSO mixture was added to the lipid solution (resulting in a 33 mole % amphotericin B solution), followed by the addition of 16.5 L of 0.9% sterile saline to the tank. The suspension was mixed with a marine propeller. The methylene chloride was removed by sterile N gas purging. The final temperature was less than 40° C. after about 13 hours. Sterile saline (7.0 L) was added to the batch for a total volume in the process vessel of about 27 L.

This product was circulated through a Gifford-Wood colloid mill for about 5 hours to decrease the average size of the lipid particles to about 5.0 um. After milling, the product was circulated through a Romicon 5.0 ceramic tangential flow filter (2 $ft^2$) using an Alfa Laval rotary lobe pump at an average flow rate of 24 gpm, for a total of about 10 hours.

Sterile physiological saline (410 L) was added in 30 L aliquots through a top port of the 140 L vessel. The average filtration rate was about 500 ml/min. The filtrate was then passed into a reservoir and concentrated by passage through a 1.2 um Romicon 2 ft² ceramic filter driven by an Alfa Laval rotary lobe pump at a flow rate of about 36 gpm (about 14.5 hours); the filtration rate was about 500–600 ml/min. This filtration removed the particles 1.2 um and less, in the filtrate. The 1.2 um retentate was collected as the final product.

EXAMPLE 24

Lipid (a 2:1 w/w/ratio of DMPC:DMPG; 20 g DMPC and 10 g DMPG) were admixed with 400 ml of 0.9% sodium chloride using a Tekmar Homogenizer, Ultra Turrex, Model SD45, (Tekmar Go., Cincinnati, Ohio) set at "high" speed, and homogenized for about 1 hour in an ice bath at about 4° C. Amphotericin B (20 g) was dissolved in 200 ml DMSO, and slowly added to the lipid, while homogenizing. The lipid and amphotericin B were homogenized for 30 minutes, until the particle size was reduced to about 1 um to about 10 um as measured by Malvern Particle size analysis.

The resulting lipid particles (HDLCs) are size selected according to the methods of tangential flow filtration as in Example 23.

We claim:

1. A composition comprising a bioactive agent-lipid complex ("HDLC"), wherein the HDLC is a non-liposomal structure having no captured volume, the lipid comprises a phospholipid, and the concentration of the bioactive agent in the complex is at least about 6 mole percent, the bioactive agent is a polyene antifungal antibiotic, the complex is substantially free of liposomes and The toxicity of the bioactive agent in the complex is less than the toxicity of the free form of the bioactive agent.

2. The composition of claim 1 wherein the phospholipid is a a saturated phospholipid.

3. The composition of claim 2 wherein the saturated phospholipid comprises a phosphatidylcholine and a phosphatidylglycerol.

4. The composition of claim 3 wherein the phosphatidylcholine is dimyristoylphosphatidylcholine and the phosphatidylglycerol is dimyristoylphosphatidylglycerol.

5. The composition of claim 3 wherein the phosphatidylcholine and the phosphatidylglycerol are in a mole ratio of about 7:3.

6. The composition of claim 1 wherein the concentration of the polyene antifungal agent in the complex is between about 6 and 50 mole percent.

7. The composition of claim 6 wherein the concentration of the polyene antifungal agent in the complex is between about 25 and 50 mole percent.

8. The composition of claim 7 wherein the concentration of the polyene antifungal agent in the complex is about 33 mole percent.

9. The composition of claim 1 wherein the antifungal agent is amphotericin B.

10. The composition of claim 9 wherein the concentration of amphotericin B in the complex between about 6 and 50 mole percent.

11. The composition of claim 10 wherein the concentration of the amphotericin B in the complex is between about 25 and 50 mole percent.

12. The composition of claim 1 wherein the antifungal agent is nystatin.

13. A pharmaceutical composition comprising the HDLC of claim 1 and a pharmaceutically acceptable carrier or diluent.

14. The pharmaceutical composition of claim 13 which is adapted for parenteral administration in the form of a sterile aqueous suspension.

15. The pharmaceutical composition of claim 13 wherein the polyene antifungal antibiotic is amphotericin B.

16. The pharmaceutical composition of claim 15 wherein the concentration of the amphotericin B in the complex is between about 25 and 50 mole percent.

17. The pharmaceutical composition of claim 13 wherein the size of the HDLC is between about 0.2 and about 10 microns.

18. The pharmaceutical composition of claim 17 wherein the antifungal agent is nystatin.

19. A method for treating an infectious disease comprising administering to a mammal in need of such treatment an anti-infectious disease-effective amount of the pharmaceutical composition of claim 13.

20. The method of claim 19 wherein the infectious disease is a fungal infection.

21. The method of claim 19 wherein the infectious disease is a vital infection.

22. A composition comprising a bioactive agent-lipid complex ("HDLC"), wherein the bioactive agent is a polyene antifungal antibiotic, the lipid comprises a phospholipid, the complex has no captured volume and is substantially free of liposomes, and wherein the concentration of the bioactive agent in the complex is from about 25 mole percent to about 50 mole percent.

23. The composition of claim 22, wherein the antibiotic is amphotericin B and the phospholipid comprises dimyristoyl phosphatidylcholine and dimyristoyl phosphatidylglycerol.

* * * * *